United States Patent
Spiegel et al.

(10) Patent No.: US 10,780,084 B2
(45) Date of Patent: Sep. 22, 2020

(54) ANTIBODY-RECRUITING MOLECULES FOR THE TREATMENT OF CANCER

(71) Applicants: YALE UNIVERSITY, New Haven, CT (US); KLEO PHARMACEUTICALS, INC., New Haven, CT (US)

(72) Inventors: David Spiegel, New Haven, CT (US); H. Marie Loughran, Perkasie, PA (US); Jeffrey C. Pelletier, Lafayette Hill, PA (US); Allen B. Reitz, Lansdale, PA (US); Matthew Ernest Welsch, New Haven, CT (US)

(73) Assignees: YALE UNIVERSITY, New Haven, CT (US); KLEO PHARMACEUTICALS, INC., New Haven, CT (US)

( * ) Notice: Subject to any disclaimer, the term of this patent is extended or adjusted under 35 U.S.C. 154(b) by 0 days.

(21) Appl. No.: 16/322,391

(22) PCT Filed: Aug. 3, 2017

(86) PCT No.: PCT/US2017/045236
§ 371 (c)(1),
(2) Date: Jan. 31, 2019

(87) PCT Pub. No.: WO2018/026997
PCT Pub. Date: Feb. 8, 2018

(65) Prior Publication Data
US 2019/0192497 A1 Jun. 27, 2019

Related U.S. Application Data

(60) Provisional application No. 62/370,278, filed on Aug. 3, 2016.

(51) Int. Cl.
| | |
|---|---|
| A61K 31/454 | (2006.01) |
| A61K 45/06 | (2006.01) |
| A61P 35/04 | (2006.01) |
| A61K 47/55 | (2017.01) |
| C07D 261/20 | (2006.01) |
| A61P 35/00 | (2006.01) |
| C07D 211/26 | (2006.01) |
| A61P 35/02 | (2006.01) |
| C07D 413/04 | (2006.01) |
| C07D 413/14 | (2006.01) |
| C07D 211/62 | (2006.01) |
| A61K 9/00 | (2006.01) |

(52) U.S. Cl.
CPC ............ *A61K 31/454* (2013.01); *A61K 45/06* (2013.01); *A61K 47/55* (2017.08); *A61P 35/00* (2018.01); *A61P 35/02* (2018.01); *A61P 35/04* (2018.01); *C07D 211/26* (2013.01); *C07D 211/62* (2013.01); *C07D 261/20* (2013.01); *C07D 413/04* (2013.01); *C07D 413/14* (2013.01); *A61K 9/0019* (2013.01)

(58) Field of Classification Search
CPC .................................................... A61K 31/454
USPC ........................................................ 546/209
See application file for complete search history.

(56) References Cited

U.S. PATENT DOCUMENTS

| | | |
|---|---|---|
| 2013/0338144 A1 | 12/2013 | Meroueh |
| 2018/0155332 A1 | 6/2018 | Spiegel et al. |

FOREIGN PATENT DOCUMENTS

| | | |
|---|---|---|
| WO | 2011046946 A2 | 4/2011 |
| WO | 2012068366 A2 | 5/2012 |
| WO | 2012119079 A1 | 7/2012 |
| WO | 2013070688 A1 | 5/2013 |
| WO | 2013162757 A1 | 10/2013 |
| WO | 2013166110 A1 | 11/2013 |
| WO | 2014178878 A1 | 11/2014 |
| WO | 2017023994 A1 | 2/2017 |
| WO | 2018026997 | 2/2018 |

OTHER PUBLICATIONS

Jakobsche, C.E. et al.; Reprogramming Urokinase into an Antibody-Recruiting Anticancer Agent; ACS Chem Biol 2012, vol. 7, pp. 316-321.
Jemal, A., Siegel, R., Xu, J., Ward, E. (2010) Cancer statistics 2010, CA Cancer J. Clin. 60, 277-300.

(Continued)

*Primary Examiner* — Taofiq A Solola
(74) *Attorney, Agent, or Firm* — Henry D. Coleman; R. Neil Sudol

(57) ABSTRACT

The present invention relates to chimeric (including bifunctional) compounds, compositions comprising those compounds and methods of treating cancer in a patient or subject, especially including metastatic and other cancers where cancer cells exhibit overexpression (heightened expression) of cell surface urokinase-type plasminogen activator receptor (urokinase receptor) compared to normal (non-cancerous) cells. The compounds bind to the urokinase-type plasminogen activator receptor (uPAR) on the surface of a cancer cell, including a metastatic cancer cell, and consequently recruit native antibodies of the patient or subject where the antibodies can selectively degrade and/or deactivate targeted cancer cells through antibody-dependent cellular phagocytosis and antibody-dependent cellular cytotoxicity (ADCC) and/or complement dependent cytotoxicity (CDC) against a large number and variety of cancers, thus providing cancer cell death and an inhibition of growth, elaboration and/or metastasis of the cancer, including remission and cure of the patient's cancer.

20 Claims, No Drawings

(56) References Cited

OTHER PUBLICATIONS

Garbe, C., Eigentler, T. K., Keilholz, U., Hauschild, A., Kirkwood, J. M. (2011) Systematic review of medical treatment in melanoma: current status and future prospects, The Oncologist 16, 5-24.

Boyle, P., Levin, B., Eds. (2008) World Cancer Report 2008, pp. 438-443, International Agency for Research on Cancer, Lyon.

Andreasen, P. A., Kjoller, L., Christensen, L., Duffy, M. J. (1997) The urokinase-type plasminogen activator system in cancer metastasis: A review, Int. J. Cancer 72, 1-22.

Duffy, M. J. (1993) Urokinase-type plasminogen activator and malignancy, Fibrinolysis 7, 295-302.

Saksela, O., Rifkin, D. B. (1988) Cell-associated plasminogen activation: Regulation and physiological functions, Ann. Rev. Cell. Biol. 4,93-126.

Del Rosso, M., Fibbi, G., Pucci, M., D'Alessio, S. A., Del Rosso, A., Magnelli, L., Chiarugi, V. (2002) Multiple pathways of cell invasion are regulated by multiple families of serine proteases, Clin. & Exp. Metastasis 19, 193-207.

Jessani, N., Liu, Y., Humphrey, M., Cravatt, B. F. (2002) Enzyme activity profiles of the secreted and membrane proteome that depict cancer cell invasiveness. Proc. Natl. Acad. Sci. U.S.A. 99, 10335-10340.

Romer, J., Nielsen, B. S., Ploug, M. (2004) The urokinase receptor as a potential target in cancer therapy, Curr. Pharm. Des. 10, 2359-2376.

Blasi, F., Carmieliet, P. (2002) uPAR: A versatile signaling orchestrator, Nat. Rev. Mol. Cell. Biol. 3, 932-943.

Duffy, M. J. (1996) Proteases as prognostic markers in cancer Clin. Cancer. Res. 1996, 2, 613-618.

Dano, K., Behrendt, N., Brunner, N., Ellis, V., Ploug, M., Pyke, C. (1994) The urokinase receptor: Protein structure and role in plasminogen activation and cancer invasion, Fibrinolysis 8 suppl 1, 189-203.

Quax, P. H. A., van Muijen, G. N. P., Weening-Verhoeff, E. J. D., Lund, L. R., Dano, K., Ruiter, D. J., Verheijen, J. H. (1991) Metastatic Behavior of human melanoma cell lines in nude mice correlates with urokinase-type plasminogen activator, its type-1 inhibitor, and urokinase-mediated matrix degradation, J. Cell. Biol. 115, 191-199.

Madsen, M. A., Deryugina, E. I., Niessen, S., Cravatt, B. F., Quigley, J. P. (2006) Activity-based protein profiling implicates urokinase activation as a key step in human fibrosarcoma intravasation, J. Biol. Chem. 281, 15997-16007.

Sier, C. F., Stephens, R., Bizik, J., Mariani, A., Bassan, M., Pedersen, N., Frigerio, L., Ferrari, A., Dano, K., Brünner, N., Blasi, F. (1998) The level of urokinase-type activator receptor is increased in serum of ovarian cancer patients, Cancer Res. 58, 1843-1849.

Harbeck, N., Kates, R. E., Gauger, K., Willems, A., Kiechle, M., Magdolen, V., Schmitt, M. (2004) Urokinase-type plasminogen activator (uPA) and its inhibitor PAI-1: Novel tumor-derived factors with a high prognostic and predictive impact in breast cancer, Thromb. Haemost. 91, 450-456.

Duffy, M. J., O'Grady, P., Devaney, D., O'Siorain, L., Fennelly, J. J., Lijnen, H. J. (1998) Urokinase-plasminogen activator, a marker for aggressive breast carcinomas, Cancer 62, 531-533.

Herszenyi, L., Plebani, M., Carraro, P., de Paoli, M., Roveroni, G., Cardin, R., Tulassay, Z., Naccarato, R., Farinati, F. (1999) The role of cystein and serine proteases in colorectal carcinoma, Cancer 86, 1135-1142.

Harvey, S. R., Hurd, T. C., Markus, G., Martinick, M. I., Penetrante, R. M., Tan, D., Venkataraman, P., DeSouza, N., Sait, S. N. J., Driscoll, D. L., Gibbs, J. F. (2003) Evaluation of urinary plasminogen activator, its receptor, matrix metalloproteinase-9 and von Willebrand factor in pancreatic cancer, Clin. Cancer Res. 9, 4935-4943.

Konecny, G., Untch, M., Pihan, A., Kimmig, R., Gropp, M., Stieber, P., Hepp, H., Slamon, D., Pegram, M. (2001) Association of urokinase-type plasminogen activator and its inhibitor with disease progression and prognosis in ovarian cancer, Clin. Cancer Res. 7, 1743-1749.

Schmitt, M., Wilhelm, O. G., Reuning, U., Krüger, A., Harbeck, N., Lengyel, E., Graeff, H., Gänsbacher, B., Kessier, H. Bürgle, M., Stürzebecher, J., Sperl, S. Magdolen, V. (2000) The urokinase-type plasminogen activator system as a novel target for tumor therapy, Fibrinolysis & Proteolysis 14, 114-132.

Ertongur, S., Lang, S., Mack, B., Wosikowski, K., Muehlenweg, B., Gires, O. (2004) Inhibition of the invasion capacity of carcinoma cells by WX-UK1, a novel synthetic inhibitor of the urokinase-type plasminogen activator system, Int. J. Cancer 2004, 110, 815-824.

Ossowski, L., Reich, E. (1983) Antibodies to plasminogen activator inhibit human tumor metastasis, Cell 35, 611¬¬-319.

Liu, S., Aaronson, H., Mitola, D. J., Leppla, S. H., Bugge, T. H. (2003) Potent antitumor activity of a urokinase-activated engineered anthrax toxin, Proc. Natl. Acad. Sci. U.S.A. 100, 657-662.

Min, H. Y., Doyle, L., V., Vitt, C. R., Zandonella, C. L., Stratton-Thomas, J. R., Shuman, M. A., Rosenberg, S. (1996) Urokinase receptor antagonists inhibit angiogenesis and primary tumor growth in syngeneic mice, Cancer Res. 56, 2428-2433.

Vallera, D. A., Li, C., Jin, N., Mortari-Panoskaltsis, A., Hall, W. A. (2002) Targeting urokinase-type plasminogen activator receptor on human glioblastoma tumors with diphtheria toxin fusion protein DTAT, J. Natl. Cancer Inst. 94, 597-606.

Spiegel, D. A. (2010) Synthetic immunology to engineer human immunity, Nat. Chem. Biol. 6, 871-872.

Murelli, R. P., Zhang, A. X., Michel, J., Jorgensen, W. L., Spiegel, D. A. (2009) Chemical control over immune recognition: A class of antibody-recruiting small molecules that target prostate cancer, J. Am. Chem. Soc. 131, 17090-17092.

Lu, Y., Low, P. S. (2002) Folate targeting of haptens to cancer cell surfaces mediates immunotherapy of syngeneic murine tumors, Cancer Immunol. Immunother. 51, 153-162.

Lu, Y., Sega, E., Low, P. S. (2005) Folate receptor-targeted immunotherapy: Induction of humoral and cellular mmunity against hapten-decorated cancer cells, Int. J. Cancer 116, 710-719.

Popkov, M., Gonzalez, B., Sinha, S. C., Barbas, C. F., III. (2009) Instant immunity through chemically programmable vaccination and covalent self-assembly Proc. Natl. Acad. Sci. U.S.A. 106, 4378-4383.

Carlson, C. B., Mowery, P., Owen, R. M., Dykhuizen, E. C., Kiessling, L. L. (2007) Selective tumor cell targeting using low-affinity, multivalent interactions, ACS Chem. Biol. 2, 119-127.

Ortega, E., Kostovetzky, M., Larralde, C. (1984) Natural DNP-binding immunoglobulins and antibody multispecificity, Mol. Immunol. 21, 883-888.

Kettner, C., Shaw. E. (1981) Inactivation of trypsin-like enzymes with peptides of arginine chloromethyl ketone, Methods Enzymol. 80, 826-842.

Spraggon, G., Phillips, C., Nowak, U. K., Ponting, C. P., Saunders, D., Dobson, C. M., Stuart, D. I., Jones, E. Y. (1995) The crystal structure of the catalytic domain of human urokinase-type plasminogen activator, Structure 3, 681-691.

Williams, E. B., Krishnaswamy, S., Mann, K. G. (1989) Zymogen/enzyme discrimination using peptide chloromethyl ketones, J. Biol. Chem. 264, 7536-7545.

Walker, B., Elmore, D. T. (1984) The behaviour of urokinase and porcine kidney cell plasminogen activator towards some synthetic peptides Thromb. Res. 34, 103-107.

Binnema, D. J., van Iersel, J. J. L., Dooijewaard, G. (1986) Quantitation of urokinase antigen in plasma and culture media by use of an ELISA, Thromb. Res. 43, 569-577.

Rajagopal, V., Kreitman, R. J. (2000) Recombinant toxins that bind to the urokinase receptor are cytotoxic without requiring binding to the alpha2-macroglobulin receptor. J. Biol. Chem. 275, 7566-7573.

Bracher, M., Gould, H. J., Sutton, B. J., Dombrowicz, D., Karagiannis, S. N. (2007) Three-colour flow cytometric method to measure antibody-dependent tumour cell killing by cytotoxicity and phagocytosis, J. Immunol. Methods 323, 160-171.

Boltz-Nitulescu, G., Willheim, M., Spiffier, A., Leutmezer. F., Tempfer, C., Winkler, S. (1995) Modulation of IgA, IgE, and IgG Fc receptor expression of human mononucler phagocytes by 1alpha,25-dihydroxyvitamin D3 and cytokines, J. Leuko. Biol. 58, 256-262.

Lu, Yingjuan, Klein, P. J., Westrick, E., Xu, L.-C., Santhapuram, H. K. R., Bloomfield, A., Howard, S. J., Vlahov, I. R., Ellis, P. R., Low,

(56) References Cited

OTHER PUBLICATIONS

P. S., Leamon, C. P. (2009) Strategy to prevent drug-related hypersensitivity in folate-targeted hapten mmunotherapy of cancer, AAPS J. 2, 628-638.

Kute, T. E., Savage, L., Stehle, J. R. Jr., Kim-Shapiro, J. W., Blanks, M. J., Wood, J., Vaughn, J. P. (2009) Breast tumor cells isolated from in vitro resistance to trastuzumab remain sensitive to trastuzumab anti-tumor effects in vivo and to ADCC killing, Cancer Immunol. Immunother. 58, 1887-1896.

Zhu, J., Wang, X., Xu, X., Abassi, Y. A. (2006) Dynamic and label-free monitoring of natural killer cell cytotoxic activity using electronic cell sensor arrays, J. Immunol. Methods 309, 25-33.

Weiner, G. J. (2007) Monoclonal antibody mechanisms of action in cancer, Immunol. Res. 39, 271-278.

Harris, T. D., Kalogeropoulos, S., Nguyen, T., Dwyer, G., Edwards, D. S., Liu, S., Bartis, J., Ellars, C., Onthank, D., Yalamanchili, P., Heminway, S., Robinson, S., Lazewatsky, J., Barrett, J. (2006) Bioconj. Chem. 17, 1294.

Sadakibara, S., Inukai, N. (1964) A New Reagent for the p-Nitrophenylation of Carboxylic Acids. Bull. Chem. Soc. Jap. 37, 1231.

Rueping, M., Mahajan, Y. R., Jaun, B., Seebach, D. (2004) Design, Synthesis and Structural Investigations of a Beta-Peptide Forming a 3(14)-Helix Stabilized by Electrostatic Interactions. Chem. Eur. J. 10, 1607.

Yu, N., Atienza, J. M., Bernard, J., Blanc, S., Zhu, J., Wang, X., Xu, X., Abassi, Y. A. (2006) Anal. Chem. 78, 35.

Blasi, F., Carmeliet, P. (2002) uPAR: A versatile signaling orchestrator, Nat. Rev. Mol. Cell. Biol, 3, 932-943.

Harbeck, N., Kates, R. E., Gauger, K., Willems, A., Kiechle, M., Magdalen, V., Schmitt, M. (2004) Urokinase-type plasminogen activator (uPA) and its inhibitor PAI-1: Novel tumor-derived factors with a high prognostic and predictive impact in breast cancer, Thromb. Haemost. 91, 450-456.

Ossowski, L., Reich, E. (1983) Antibodies to plasminogen activator inhibit human tumor metastasis, Cell 35, 611¬¬-619.

Lu, Y., Sega, E., Low, P. S. (2005) Folate receptor-targeted immunotherapy: Induction of humoral and cellular immunity against hapten-decorated cancer cells, Int. J. Cancer 116, 710-719.

Boltz-Nitulescu, G., Wilhelm, M., Spiffier, A., Leutmezer. F., Tempfer, C., Winkler, S. (1995) Modulation of IgA, IgE, and IgG Fc receptor expression of human mononucler phagocytes by 1alpha,25-dihydroxyvitamin D3 and cytokines, J. Leuko. Biol. 58, 256-262.

Lu, Yingjuan, Klein, P. J., Westrick, E., Xu, L.-C., Santhapuram, H. K. R., Bloomfield, A., Howard, S. J., Vlahov, I. R., Ellis, P. R., Low, P. S., Leamon, C. P. (2009) Strategy to prevent drug-related hypersensitivity in folate-targeted hapten immunotherapy of cancer, AAPS J. 2, 628-638.

Yu, N., Atlenza, J. M., Bernard, J., Blanc, S., Zhu, J., Wang, X., Xu, X., Abassi, Y. A. (2006) Anal. Chem. 78, 35.

ANTIBODY-RECRUITING MOLECULES FOR THE TREATMENT OF CANCER

This application is a United States national phase patent application based upon international patent application number PCT/US2017/045236 of international filing date Aug. 3, 2017, which claims the benefit of priority of U.S. provisional application No. 62/370,278 filed Aug. 3, 2016 entitled "Antibody-Recruiting Agent for the Treatment of Cancer", the entire contents of said two related applications being incorporated by reference herein.

RELATED APPLICATIONS AND GRANT SUPPORT

This invention was made with government support under 1DP2OD002913-01 awarded by the National Institute of Health. The government has certain rights in the invention.

FIELD OF THE INVENTION

The present invention relates to chimeric (including bifunctional) compounds, compositions comprising those compounds and methods of treating cancer in a patient or subject, especially including metastatic cancer and other cancers where cancer cells exhibit overexpression (heightened expression) of cell surface urokinase-type plasminogen activator receptor (urokinase receptor) compared to normal (non-cancerous) cells. The compounds bind to the urokinase-type plasminogen activator receptor (uPAR) on the surface of a cancer cell, including a metastatic cancer cell, and consequently recruit native antibodies of the patient or subject where the antibodies can selectively remove, destroy, clear and/or deactivate targeted cancer cells through antibody-dependent cellular phagocytosis (ADCP), antibody-dependent cellular cytotoxicity (ADCC), complement dependent cytotoxicity (CDC) and/or other immune effector mechanisms against a large number and variety of cancers, thus providing cancer cell death and an inhibition of growth, elaboration and/or metastasis of the cancer, including remission and cure of the patient's cancer.

INTRODUCTION/BACKGROUND OF THE INVENTION

Cancer is currently the second leading cause of death in the United States. Metastatic cancers are especially difficult to treat and are associated with higher levels of mortality compared to benign tumors. American men and women have a 38-44% chance of developing invasive cancers over the course of their lifetimes. Tumor metastasis involves cancer cell invasion of surrounding tissues, often accelerated by cell suffice proteases. One such protease known as the urokinase-type plasminogen activator (uPA) is capable of breaking down extracellular matrix proteins and activating migration-inducing signal cascades through binding to the urokinase-type plasminogen activator receptor (uPAR).

A large body of evidence suggests that uPA and uPAR expression are substantially higher on invasive malignant cancer cells than on healthy cells or benign tumors. In clinical settings, high levels of uPAR are used as diagnostic measures for metastatic potential and poor clinical outcome in several malignancies. Novel strategies to combat cancer are highly desirable due to the limitations of the more traditional treatment options, including radiation therapy and chemotherapy. These treatment methods are not only associated with significant side effects but are also limited with respect to their effectiveness in the treatment of late stage cancers.

The ability to target cancer cells selectively is thus of great importance, with the potential to significantly reduce toxicity and off-target effects, thereby reducing side effects experienced by the patient. New approaches to treat cancer that combine the advantages of traditional small molecules and biologics could address many of the limitations associated with currently available therapies.

Anthroquinone-based small molecules have been identified previously as potential anti-cancer agents and have been shown to bind to OAR in vitro with affinity capable of blocking cancer cell invasion, migration, and adhesion. Previously, the development of an antineoplastic antibody-recruiting agent equipped with the urokinase protein as a uPAR target-binding domain has been reported. (*ACS Chem. Biol.* 2012, 7, 316). The molecules disclosed here are expected to target uPAR-over-expressing A172 glioblastoma cells and facilitate antibody-dependent cellular phagocytosis (ADCP).

BRIEF DESCRIPTION OF THE INVENTION

The present invention is directed to compounds according to the general formula:

TBT-LINKER-ABT

Where TBT is a moiety which binds to an active site of urokinase-type plasminogen activator receptor (uPAR) on the surface of cancer cells of a patient or subject;
ABT is an antibody binding moiety comprising a hapten which is capable of binding to an antibody in said patient or subject;
or a pharmaceutically acceptable salt, stereoisomer, enantiomer, solvate or polymorph thereof.

In one embodiment of the invention, the TBT is selected from a moiety according to the general formulae:

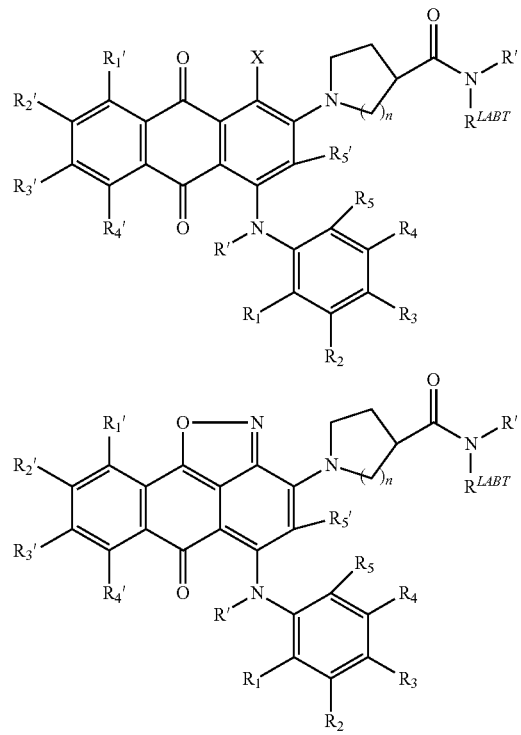

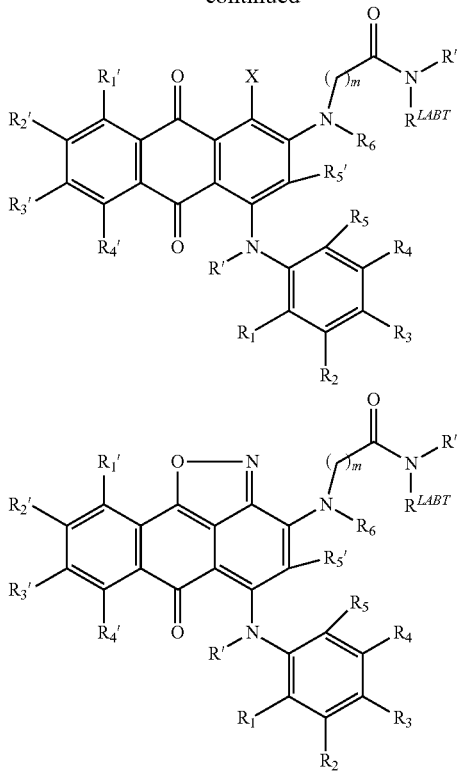

Wherein X=H, F, Cl, Br, CF$_3$, MeSO$_2$, CH$_3$O, CF$_5$O N(R$^N$)$_2$, where each R$^N$ is independently H or a C$_1$-C$_3$ alkyl group;
R$_1$, R$_2$, R$_3$, R$_4$ and R$_5$ are each independently H, a halogen (F, Cl, Br, preferably F), a C$_1$-C$_3$ alkyl group optionally substituted with one or two hydroxyl groups or up to three fluoro groups, NO$_2$, CN, a (CH$_2$)$_m$, OR$^E$ (O-alkyl) group, a (CH$_2$)$_m$COR$^E$ (keto) group, a (CH$_2$)$_m$COOR$^E$ (carboxy ester) group, a (CH$_2$)$_m$SO$_3$H group, a (CH$_2$)$_m$OCOR$^E$ (oxycarbonyl ester) group,

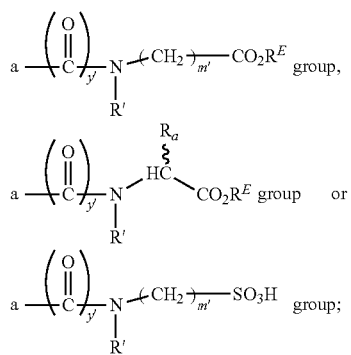

Each R' is independently H or a C$_1$-C$_3$ alkyl group (preferably H or CH$_3$, most often H);
R$_a$ is a sidechain derived from a natural or unnatural amino acid (D- or L-, preferably a L-amino acid) preferably selected from the group consisting of alanine (methyl), arginine (propyleneguanidine), asparagine (methylenecarboxiamide), aspartic acid (ethanoic acid), cysteine (thiol, reduced or oxidized di-thiol), glutamine (ethylcarboxy- amide), glutamic acid (propanoic acid), histidine (methyleneimidazole), isoleucine (1-methylpropane), leucine (2-methylpropane), lysine (butyleneamine), methionine (ethylmethylthioether), phenylalanine (benzyl), proline (R' forms a cyclic ring with R$_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or value (isopropyl)

Each E$^E$ is H or a C$_1$-C$_6$ alkyl group optionally substituted with one or two hydroxyl groups or up to three chloro or fluoro groups (preferably R$^E$ is H or a C$_1$-C$_3$ alkyl group);

R$_1'$, R$_2'$, R$_3'$, R$_4'$ and R$_5'$ are each independently H, a halogen (F, Cl, Br, I, preferably F), a C$_1$-C$_6$ (preferably C$_1$-C$_3$) alkyl group optionally substituted with one or two hydroxyl groups or up to three chloro or fluoro groups, NO$_2$, CN, a (CH$_2$)$_m$OR$^E$ (O-alkyl) group, a (CH$_2$)$_m$COOR$^E$ (carboxy ester) group, a (CH$_2$)$_m$O—COR$^E$ (oxycarbonyl ester) group or a (CH$_2$)$_m$COR$^E$ (keto) group;

R$_1$ is H or SO$_3$H, R$_2$ is H, CO$_2$H, SO$_3$H, —NHCH$_2$—CO$_2$H, —NHCH$_2$—SO$_3$H, —C(O)—NHCH$_2$—CO$_2$H or —C(O)—NHCH$_2$—SO$_3$H, R$_3$ is H, CO$_2$H, or SO$_3$H, R$_4$ is H, CO$_2$H, SO$_3$H, and R$_5$ is H, CO$_2$H, or SO$_3$H, or a pharmaceutically acceptable salt or solvate thereof.

Each m' is independently 0, 1, 2, 3, 4, 5, or 6 (preferably 0, 1, 2 or 3, more preferably 0 or 1);
Each y' is independently 0, 1 or 2 (preferably 0 or 1;
R$^{LABT}$ is a LIN-ABT group,
n=0-4,
m=0-5, preferably 3-5, and
R$_6$H, C1-C4 lower alkyl.

In one embodiment of the invention, the ABT is an antibody bonding moiety comprising a hapten which is capable of binding to an antibody in said patient or subject, or a pharmaceutically acceptable salt, stereoisomer, enantiomer, solvate or polymorph thereof.

In one embodiment of the invention, compounds of the present invention include those compounds where TBT-LIN-ABT are as follows:

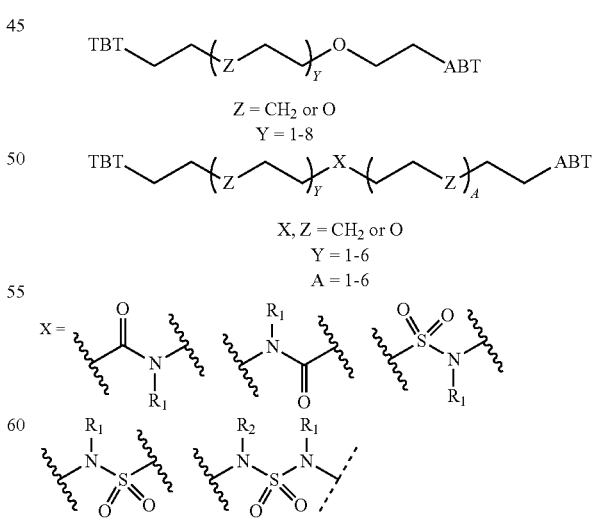

R1, R2 same or different from H, C1-3 lower hydroxyalkyl and aminoalkyl

-continued
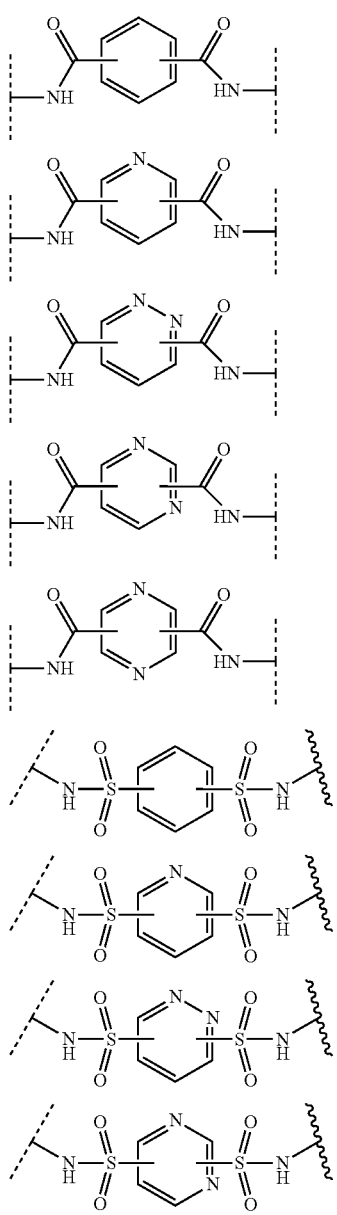
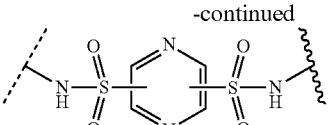
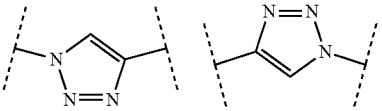
Y = CH, N
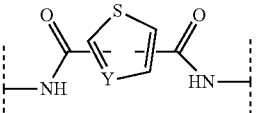
Y = CH, N
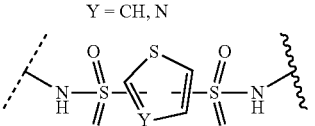
Z = CH or O
Y = 1-6
K = O, NR$_3$
A = 0-3; R$_3$ = H, C1-C3
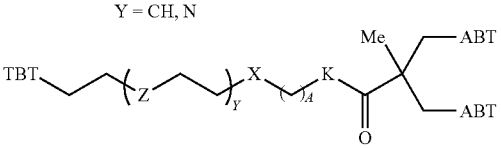
Z = CH or O
Y = 1-6
K, K$_1$ = O or NR$_3$
A = 0-3; R$_3$ = H, C1-C3
In one embodiment of the invention, compounds of the present invention include those compounds wherein LIN-ABT is
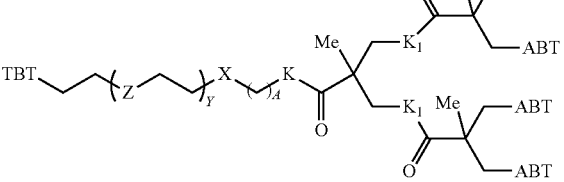
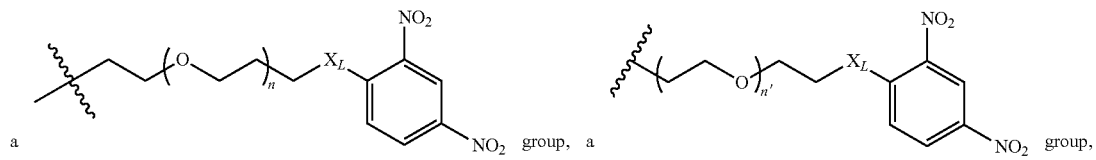
group, a 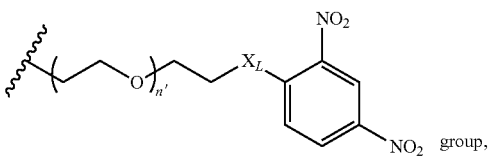 group,
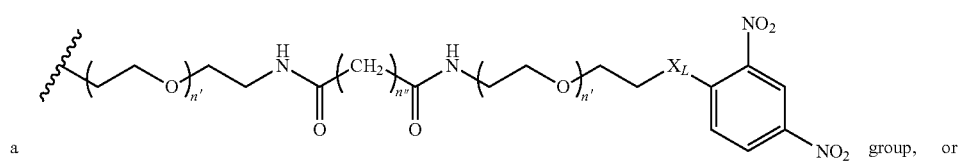
group, or

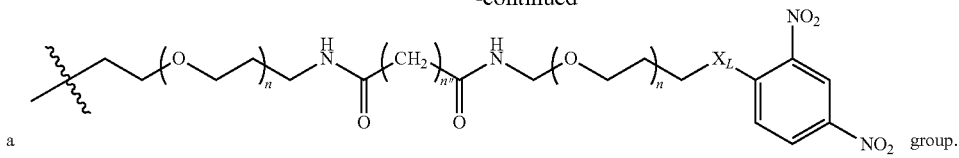 group.

Where $X_L$ is $N(R^1)$, O, S, S(O), $SO_2$, $S(O)_2O$, $-OS(O)_2$, or $OS(O)_2O$ (preferably $N(R^1)$ or O, more preferably $N(R^1)$); and $R^1$ is H, a $C_1$-$C_3$ alkyl group or a $-C(O)(C_1$-$C_3)$ group, preferably H; each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, or 8; and each n" is independently 0 to 8, often 1 to 7, or 1, 2, 3, 4, 5 or 6 (preferably 3).

In one embodiment of the invention, compounds of the present invention include those compounds where LIN is a linker group according to the chemical structure:

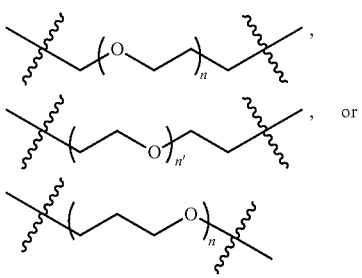

Where each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, or 8; and each n" is independently 0 to 8, often 1 to 7, or 1, 2, 3, 4, 5 or 6 (preferably 3).

In one embodiment of the invention, compounds of the present invention include those compounds wherein LIN is a group according to the chemical structure:

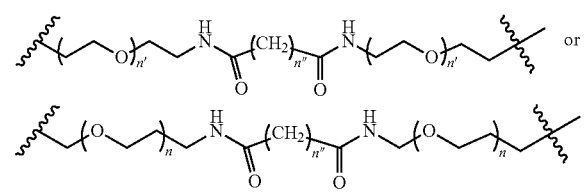

Where each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, or 8; and each n" is independently 0 to 8, often 1 to 7, or 1, 2, 3, 4, 5 or 6 (preferably 3);

Where n is about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc., or a linker according to the chemical structure:

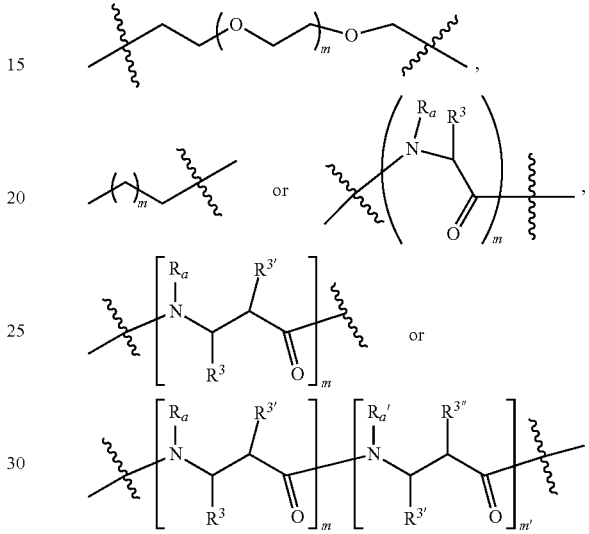

Where $R_a$ and $R_{a'}$ are each independently H, $C_1$-$C_3$ alkyl, alkanol, aryl or benzyl or form a cyclic ring with $R^3$ (proline) and $R^3$, $R^{3'}$ and $R^{3''}$ are each independently a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl); and m and m' (within the context of this use) is each independently an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 2, 3, 4 or 5.

In one embodiment of the invention, compounds of the present invention include those compounds wherein LIN is a group according to the chemical formula:

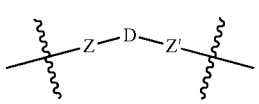

Where Z and Z' are each independently a bond, $-(CH_2)_i-$O, $-(CH_2)_i-$S, $-(CH_2)_i-$N—R, <img>

Wherein said —$(CH_2)_i$ group, if present in Z or Z', is bonded to a connector (CT), an alternative linker, $A_BM$ and/or $UPAR_BM$;

Each R is H, or a $C_1$-$C_3$ alkyl or alkanol group;

Each $R^2$ is independently H or a $C_1$-$C_3$ alkyl group;

Each Y is independently a bond, O, S or N—R;

Each i is independently 0 to 100, 0 to 75, 1 to 60, 1 to 55, 1 to 50, 1 to 45, 1 to 40, 2 to 35, 3 to 30, 1 to 15, 1 to 10, 1 to 8, 1 to 6, 0, 1, 2, 3, 4 or 5;

D is

<img> or a bond, with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m' is 1 to 100, 1 to 751 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 (n is preferably 2);

X' is O, S or N—R; and

R is as described above, or a pharmaceutical salt thereof.

In one embodiment of the invention, compounds of the present invention include those compounds wherein said ABT group is a group according to the chemical structure:

<img> or a group according to the chemical structure:

<img>

Where Y' is H or $NO_2$ (preferably H);

X is O, $CH_2$, $NR^1$, S(O), $S(O)_2$, —$S(O)_2O$, —$OS(O)_2$, or $OS(O)_2O$; and $R^1$ is H, a $C_1$-$C_3$ alkyl group, or a —$C(O)(C_1$-$C_3)$ group.

In one embodiment of the invention, compounds of the present invention include those compounds wherein said $A_BM$ group is a group represented by the chemical formula:

<img>

Where X' is $CH_2$, O, N—$R^{1'}$, or S, preferably O;

$R^{1'}$ is H or $C_1$-$C_3$ alkyl; and

Z is a bond, a monosaccharide, disaccharide, oligosaccharide, more preferably a sugar group selected from the monosaccharides, including aldoses and ketoses, and disaccharides, including those disaccharides described herein. Monosaccharide aldoses include monosaccharides such as aldotriose (D-glyceraldehdye, among others), aldotetroses (D-erythrose and D-Threose, among others), aldopentoses, (D-ribose, D-arabinose, D-xylose, D-lyxose, among others), aldohexoses (D-allose, D-altrose, D-Glucose, D-Mannose, D-gulose, D-idose, D-galactose and D-Talose, among others), and the monosaccharide ketoses include monosaccharides such as ketotriose (dihydroxyacetone, among others), ketotetrose (D-erythrulose, among others), ketopentose (D-ribulose and D-xylulose, among others), ketohexoses (D-Psicone, D-Fructose, D-Sorbose, D-Tagatose, among others), aminosugars, including galactoseamine, sialic acid, N-acetylglucosamine, among others and sulfosugars including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose which may have the glucose residue optionally N-acetylated), palatinose (which may have the glucose residue optionally N-acetylated), gentiobiluose (which may have the glucose residue optionally N-acetylated), mannobiose melibiose (which may have the glucose residue and/or the galactose residue optionally N-acetylated) melibiulose (which may have the galactose residue optionally N-acetylated rutinose, (which may have the glucose residue optionally N-acetylated), rutinulose and xylobiose among others.

In one embodiment of the invention, compounds of the present invention include those compounds wherein said ABT group is a group according to the chemical structure:

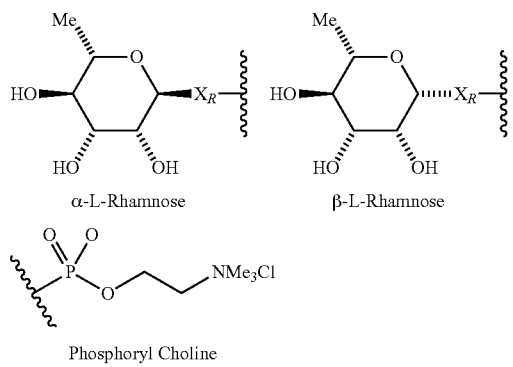

α-L-Rhamnose    β-L-Rhamnose

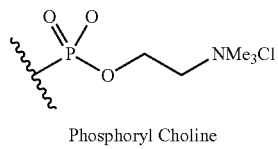

Phosphoryl Choline

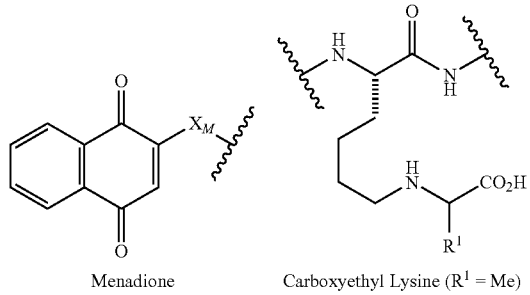

Menadione    Carboxyethyl Lysine (R¹ = Me)

Where $X_R$ is O, S or $NR^1$; and
$X_M$ is O, $NR^1$ or S, and
$R^1$ is H or a $C_1$-$C_3$ alkyl group.

In one embodiment o the invention, compound of the present invention include those compounds containing more than one rhamnose group.

In one embodiment of the invention, compounds of the present invention include those compounds wherein said ABT is a group according to the chemical structure:

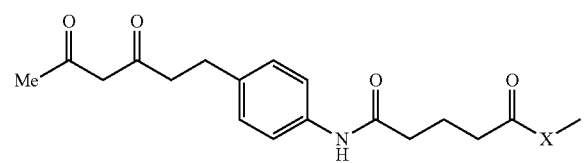

Where X" is O, $CH_2$, $NR^1$, S; and
$R^1$ is H, a $C_1$-$C_3$ alkyl group or a —$C(O)(C_1$-$C_3)$ group; or

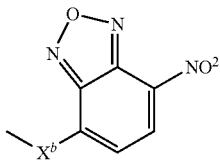

Where $X^b$ is a bond, O, $CH_2$ or $NR^1$ or S; and
$R^1$ is the same as above; or
a group according to the chemical structure:

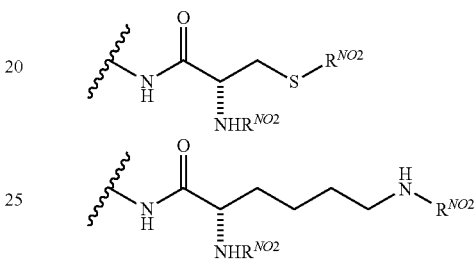

Where $R^{NO2}$ is a dinitrophenyl group optionally linked through $CH_2$, $S(O)$, $S(O)_2$, —$S(O)_2O$, —$OS(O)_2$, or $OS(O)_2O$;
a dinitrophenyl group according to the chemical structure:

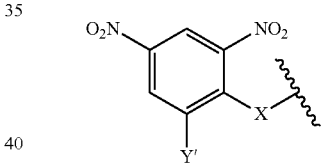

Where Y' is H or $NO_2$ (preferably H);
X is O, $CH_2$, $NR^1$, $S(O)_2$, —$S(O)_2O$, —$OS(O)_2$, or $OS(O)_2O$; and
$R^1$ is H, a $C_1$-$C_3$alkyl group, or a —$C(O)(C_1$-$C_3)$ group;

In one embodiment of the invention, compounds of the present invention include those compounds where ABT is a dinitrophenyl group or a rhamnose group.

In one embodiment of the invention, compounds of the present invention include those compounds where LIN includes the following:

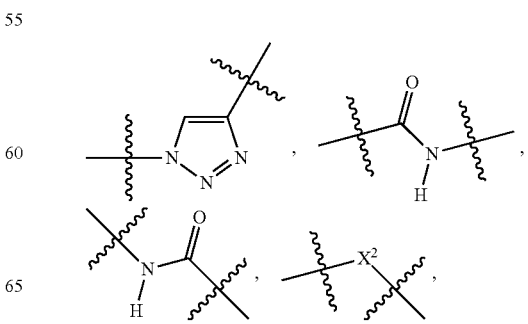

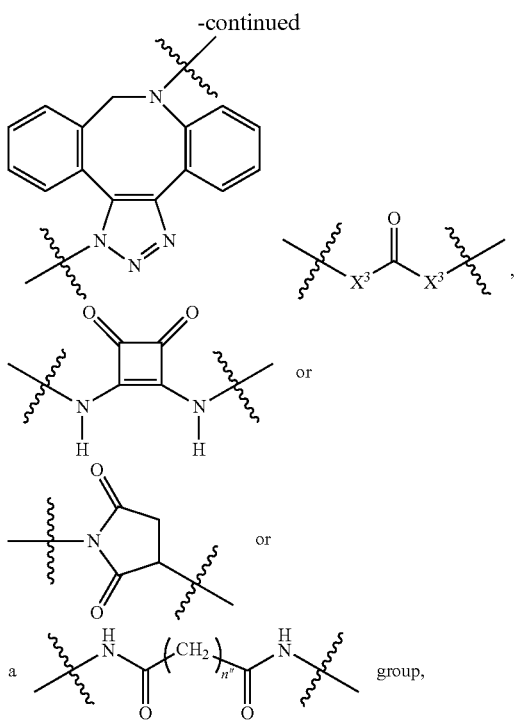

Where $X^2$ is $CH_2$, O, S, $NR^4$, S(O), $S(O)_2$, —$S(O)_2O$, —$OS(O)_2$, or $OS(O)_2O$;

$X^3$ is O, S, $NR^4$;

$R^4$ is H, a $C_1$-$C_3$ alkyl or alkanol group, or a —$C(O)(C_1$-$C_3)$ group; and n" is independently 0 to 8, often 1 to 7, or 1, 2, 3, 4, 5 or 6 (preferably 3).

In accordance with the present invention there is also provided a method of treating cancer comprising administering to a cancer patient compounds of the present invention.

In accordance with the present invention there is also provided a method of reducing the likelihood that a cancer in a patient will metastasize comprising administering to a cancer patient compounds of the present invention.

The present invention also includes the use of compounds of the present invention in the manufacture of a medicament for the treatment of cancer.

By virtue of the present invention, it may be possible to provide improved therapies for the treatment of cancer. uPAR is over-expressed on many cancer cell types which enables its potential application as a therapeutic targeting a wide range of cancer cell types. Compounds of the present invention employ a dual mode of action as an anticancer therapeutic by disrupting the native uPA uPAR interaction as an antagonist and by targeting metastatic cancer cells for destruction by the host immune system as an antibody recruiting molecule and shows that employing small molecules to redirect the cytotoxic functions of antibodies selectively against cancer cells, might reduce the toxicity associated with other cancer fighting strategies.

DETAILED DESCRIPTION OF THE INVENTION

In accordance with the present invention there may be employed conventional chemical synthetic and pharmaceutical formulation methods, as well as pharmacology, molecular biology, microbiology, and recombinant DNA techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

Furthermore, the following terms shall have the definitions set out below. It is understood that in the event a specific term is not defined hereinbelow, that term shall have a meaning within its typical use within context by those of ordinary skill in the art.

The term "compound", as used herein, unless otherwise indicated, refers to any specific chemical compound disclosed herein and includes tautomers, regioisomers, geometric isomers, stereoisomers and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enamiomerically enriched mixtures of disclosed compounds. The term also refers, within context, to prodrug forms of compounds which have been modified to facilitate the administration and delivery of compounds to a site of activity. It is noted that in describing the present compounds, numerous substituents, linkers and connector molecules and variables associated with same, among others, are described. The use of a bond presented as ----- signifies that a single bond is present or absent, depending on the context of the chemistry described. The use of a bond presented as ~~~~~~ signifies that a single bond or a double bond is intended depending on the context of the chemistry described. It is understood by those of ordinary skill that molecules which are described herein are stable compounds as generally described hereunder.

The term "patient" or "subject" is used throughout the specification within context to describe an animal, generally a mammal and preferably a human, to whom treatment, including prophylactic treatment (prophylaxis, including especially as that term is used with respect to reducing the likelihood of metastasis of an existing cancer), with the compositions according to the present invention is provided. For treatment of those infections, conditions or disease states which are specific for a specific animal such as a human patient or a patient of a particular gender, such as a human male or female patient, the term patient refers to that specific animal. Compounds according to the present invention are useful for the treatment of cancer, including especially for use in reducing the likelihood of metastasis of a cancer.

The term "effective" is used herein, unless otherwise indicated, to describe an amount of a compound or composition which, in context, is used to produce or effect an intended result, whether that result relates to the inhibition of the effects of a disease state (e.g. cancer) on a subject or the treatment or prophylaxis of a subject for secondary conditions, disease states or manifestations of disease states as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for cancer or metastasis of cancer, including improvement in the condition through lessening or suppression of at least one symptom, inhibition of cancer growth, reduction in cancer cells or tissue, prevention, reduction in the likelihood or delay in progression of cancer or metastasis of the cancer, prevention or delay in the onset of disease states or conditions which occur secondary to cancer or remission or cure of the cancer, among others. Treatment, as used herein, encompasses both prophylactic and therapeutic treatment. The term "prophylactic" when used, means to reduce the likelihood of an occurrence or the severity of an occurrence within the context of the treatment of cancer, including cancer metastasis as otherwise described hereinabove.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors.

Neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms (cancer) are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991). All of these neoplasms may be treated using compounds according to the present invention.

Representative common cancers to be treated with compounds according to the present invention include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. Because of the activity of the present compounds, the present invention has general applicability treating virtually any cancer in any tissue, thus the compounds, compositions and methods of the present invention are generally applicable to the treatment of cancer and in reducing the likelihood of development of cancer and/or the metastasis of an existing cancer.

In certain particular aspects of the present invention, the cancer which is treated is metastatic cancer, a recurrent cancer or a drug resistant cancer, especially including a drug resistant cancer. Separately, metastatic cancer may be found in virtually all tissues of a cancer patient in late stages of the disease, typically metastatic cancer is found in lymph system/nodes (lymphoma), in bones, in lungs, in bladder tissue, in kidney tissue, liver tissue and in virtually any tissue, including brain (brain cancer/tumor). Thus, the present invention is generally applicable and may be used to treat any cancer in any tissue, regardless of etiology.

The term "tumor" is used to describe a malignant or benign growth or tumefacent.

The term "antibody binding moiety", "antibody binding terminus" or "antibody binding structure" (ABT) within the general formula of compounds according to the present invention) is used to described that portion of a bifunctional compound according to the present invention which comprises at least one small molecule or hapten which can bind to antibodies within the patient. The term "hapten" is used to describe a small-molecular-weight inorganic or organic molecule that alone is not antigenic but which when linked to another molecule, such as a carrier protein (albumin, etc.) or in the case of the present invention, as an antibody terminus in the present compounds, is antigenic; and an antibody raised against the hapten (generally, the hapten bonded or complexed to the carrier) will react with the hapten alone. Because, in many instances, anti-hapten (especially anti-DNP) antibodies are already present in the human blood stream as endogenous antibodies because they naturally become raised to endogenous haptens (already present in patients), no pre-vaccination is necessary for activity, but may optionally be used to increase the efficacy of the compounds disclosed herein.

Pharmaceutical compositions according to the present invention comprise an effective amount of at least one compound as otherwise described herein, in combination with a pharmaceutically effective amount of a carrier, additive or excipient, optionally, in combination with one or more of the additional agents, especially anti-cancer agents, otherwise described herein, all in effective amounts.

The pharmaceutical compositions of the present invention may be formulated in a conventional manner using one or more pharmaceutically acceptable carriers and may also be administered in immediate, early release or controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 1 to several grams, more preferably about 1 milligram to about 750 milligrams, and even more preferably about 10 milligrams to about 500-600 milligrams of active ingredient, alone or in combination with at least one other compound according to the present invention or other anti-cancer agent which may be used to treat cancer or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male or female human) suffering from cancer can be treated by administering to the patient (subject) an effective amount of a compound according to the present invention including pharmaceutically acceptable salts, solvates or polymorphs, thereof optionally in a pharmaceutically acceptable carrier or diluent, either alone, or in combination with other known pharmaceutical agents, preferably agents which can assist in treating cancer and/or secondary effects of cancer or ameliorate the secondary effects and conditions associated with cancer, including metastasis of cancer. This treatment can also be administered in conjunction with other conventional cancer therapies, including radiation therapy.

Other agents which may be administered to a patient in combination with a compound according to the present invention (prior to, subsequently to, concurrently with or in a fixed-dose combination with) include, for example, an antimetabolite, an inhibitor of topoisomerase I and II, alkylating agent, a microtubule inhibitor or a mixture thereof, an FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody or a mixture thereof; an anticancer agent from the list of everolimus, trabectedin, abraxane, TLK 286, AV-299, DN-101, pazopanib, GSK690693, RTA 744, ON 0910.Na, AZD 6244, AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolamide, ZK-304709, seliciclib; PD0325901 AZD-6244, capecitabine, L-glutamic acid, N-[4[2-(2-amino-4,7-dihydro-4-oxo-1H-pyrrolo[2,3-d]pyrimidin-5-yl) ethyl]benzoyl]-, disodium salt, heptalaydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl]-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamie acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine hydroxyurea, idarubicin, ifosfamide, imatinib, Ieuprolide, levamisole, lomustine, mechlorethamine, melphalan, 6-mercaptopurine, mesna, methotrexate, mitomycin, mitotane, mitaxantrone, nilatamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291 squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxitne, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001 ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11 dexrazoxane, alemtuzumab, all-transretinoic acid, or a mixture thereof.

The compounds of the present invention can be administered by any appropriate route, for example, orally, parenterally, intravenously, subcutaneously, or topically, in liquid, cream, gel, or solid form, or by aerosol form.

The compounds of the present invention are typically included in the pharmaceutically acceptable carrier or diluent in an amount sufficient to deliver to a patient a therapeutically effective amount for the desired indication, without causing serious toxic effects in the patient treated. A typical dose of the active compound for the herein-mentioned conditions is in the range from about 10 ng/kg to 300 mg/kg, preferably about 0.1 to 100 mg/kg per day, more generally 0.5 to about 25 mg per kilogram body weight of the recipient/patient per day. A typical topical dosage will range from 0.01-5% wt/wt in a suitable carrier.

The compounds of the present invention are typically conveniently administered in any suitable unit dosage form, including, but not limited to one containing less than 1 mg, 1 mg to 3000 mg, preferably about 5 to 500-600 mg or more of active ingredient per unit dosage form. An oral dosage of about 25-250 mg is often convenient.

The compounds of the present invention are typically preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of the compounds of the present invention in the drug product, e.g. pharmaceutical composition, will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes: a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The compounds of the present invention can be administered as a component of an elixir, suspension, syrup, wafer, chewing gum or the like. A syrup may contain, in addition to the active compounds, sucrose as a sweetening agent and certain preservatives, dyes and colorings and flavors.

The compounds of the present invention can also be mixed with other active materials that do not impair the desired action, or with materials that supplement the desired action, such as other anticancer agent, anti-HIV agents, antibiotics, antifungals, anti-inflammatories, or antiviral compounds. In certain preferred aspects of the invention, one or more compounds according to the present invention are coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid, buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the compounds of the present invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as steamyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into, the container. The container is then swirled by hand to free lipid material from the sides of the container and to disperse lipid ageregates, thereby forming the liposomal suspension.

EXAMPLES

The following examples are provided for illustrative purposed and are not intended to limit the scope of the invention of the claims. Certain references to compounds, e.g., as "ABT-1", or "ARM-U2 derivative 6-ABT-5 was synthesized as described for 6-ABT-1" are made with reference to the compounds and procedures set forth and described in WO2017/023994, published Feb. 9, 2017, the disclosure of which is hereby incorporated by reference.

General Chemical Synthesis

The following chemical example is provided to indicate to one skilled in the art as to how to make certain compounds in accordance with the present invention. N-Boc-nipecotic acid 1 was coupled with the suitable DNP linked amine using HATU coupling conditions, and the Boc group was removed with TFA to give 2. The secondary amine of 2 displaced the bromine of 3 at 70° C. with DIPEA in DMF to give 4. Upon exposure of a red solution of the isoxazole 4 in DMSO to room light for up to 48 h or longer, a color change to purple is observed giving 5. The conversion of 4 to 5 occurs much more quickly in aqueous solution ($t_{1/2} \approx 3$ h) relative to DMSO ($t_{1/2} \approx 24$ h). HPLC purification resulted in isolation of the ring opened compound 5.

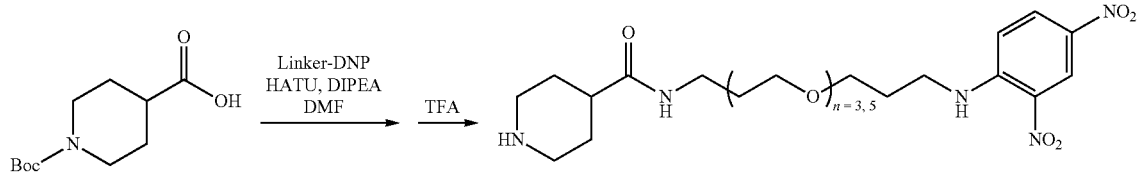

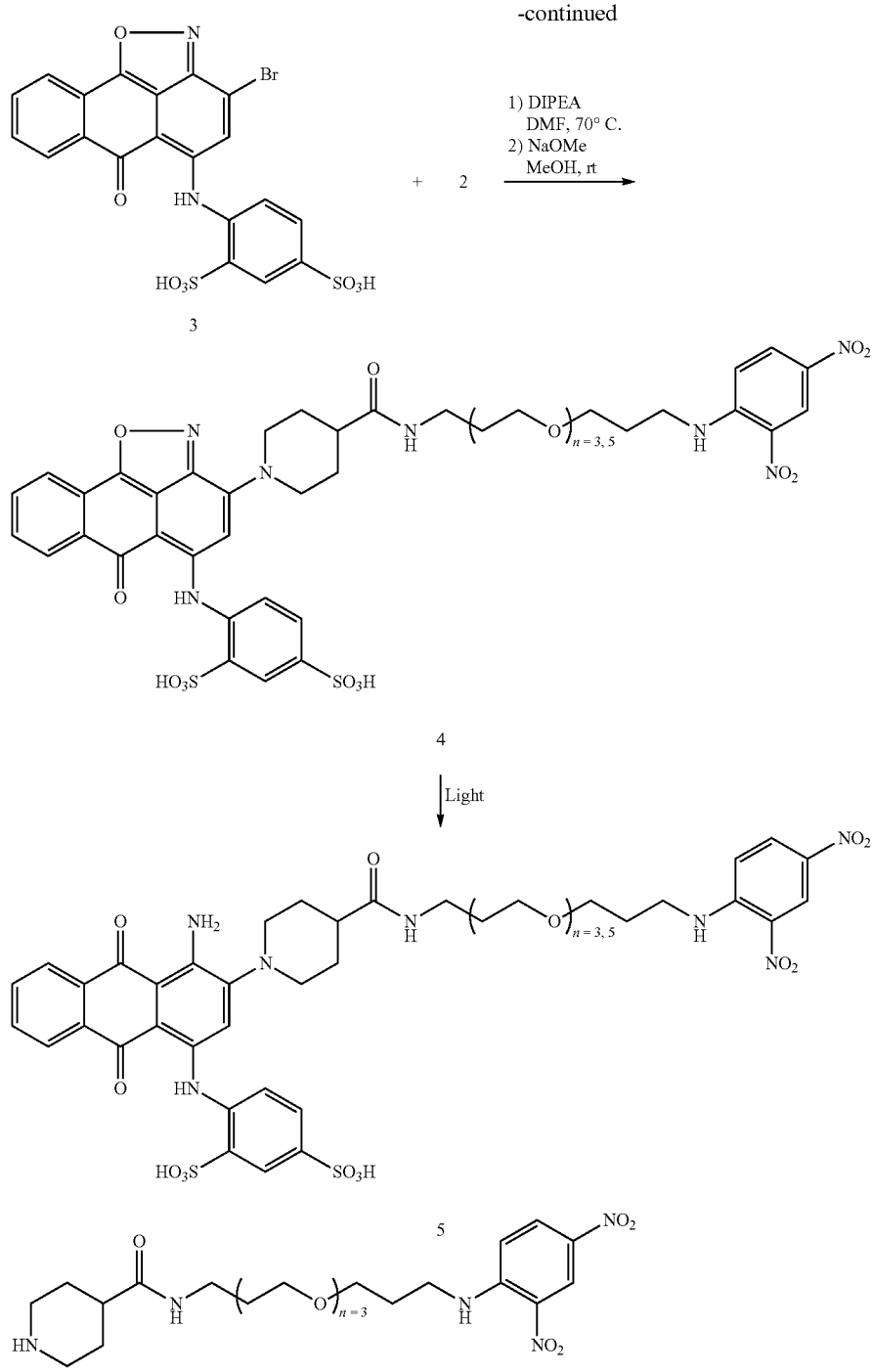

Synthesis of ABT-5

ABT-5 was synthesized in a similar manner to ABT-1 but using 1-BOC-piperidine-4-carboxylic acid in place of BOC-D-nipecotic acid or BOC-L-nipecotic acid. First, 1-chloro-2,4-dinitrobenzene was coupled to 4,7,10-tridecanediaime as previously described (REF). The resulting DNP appended PEG3-linker (2.17 g, 5.62 mmol), 1.-BOC-piperidine-4-carboxylic acid (1.17 g, 5.11 mmol), EDC (1.08 g, 5.62 mmol), HOAt (0.76 g, 5.62 mmol), and DIPEA (979 µL, 5.62 mmol) were combined in DMF (10 mL) and stirred overnight at room temperature. The reaction was diluted with ethyl acetate, washed with water (2×), 1N HCl, and 1M Na2CO3. The organic layer was dried over Na2SO4, filtered and concentrated in vacuo. The crude BOC-protected ABT-5 was dissolved in a 1:1 DCM/TFA and stirred at room temperature for 4 hours. The volatiles were removed in vacuo. The residue was diluted with DCM and carefully neutralized with sat. aq. NaHCO3. The layers were separated and the aqueous layer was extracted twice more with DCM. The combined organic extracts were dried over Na2SO4, filtered and concentrated to yield crude ABT-5 (2.03 g 4.08 mmol, 80% yield) as a viscous yellow oil. ES-LCMS: m/z 498.09 (M+H)+.

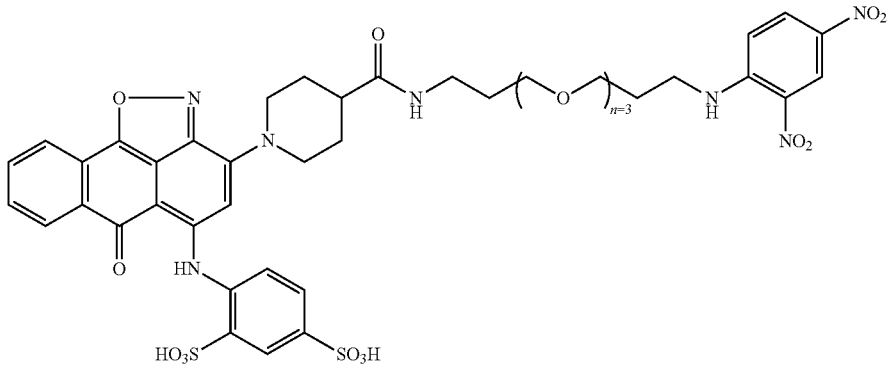

Synthesis of ARM-U2 Derivative 6-ABT-5

ARM-U2 derivative 6-ABT-5 was synthesized as described for 6-ABT-1 only intermediate VIIII (15 mg, 0.027 mmol) was coupled to linker ABT-5 (13.5 mg, 0.027 mmol) as opposed to ABT-1. The product was purified by Gilson C18 reverse phase prep HPLC with a gradient of 20-70% ACN/H2O (both water and ACN contain 0.1% TFA) and following lyophilization yielded 6-ABT-5 in 29% yield (7.6 mg, 0.0079 mmol) as a lyophilized reddish-orange solid. $^1$H NMR (300 MHz, DMSO) δ 11.68 (s, 1H), 8.87-9.03 (m, 1H), 8.77-8.83 (m, 1H), 8.39-8.58 (m, 1H), 8.18-8.26 (m, 1H), 8.09-8.18 (m, 2H), 7.76-7.86 (m, 2H), 7.66-7.73 (m, 1H), 7.60-7.65 (m, 1H), 7.52-7.58 (m, 1H), 7.17-7.25 (m, 1H), 6.33-6.39 (m, 1H), 4.31-4.52 (m, 2H), 3.46-3.60 (m, 17H), 3.01-3.12 (m, 2H), 1.86 (s, 4H), 1.67-1.79 (m, 2H), 1.60 (s, 2H). ES-LCMS: in m/z 968.30 (M+H)$^{30}$.

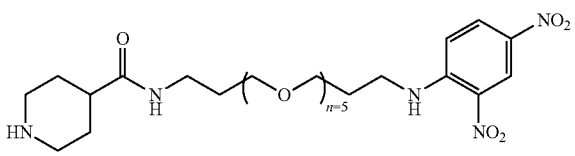

Synthesis of ABT-6

ABT-6 was synthesized in similar manner to ABT-5 only that 1-chloro-2,4-dinitrobenzene was coupled to 1,19-diamino-4,7,10,13,16-pentaoxanonadecane instead of 4,7,10-tridecanediaime to synthesize the DNP appended PEG5-linker. ES-LCMS: m/z 586.33

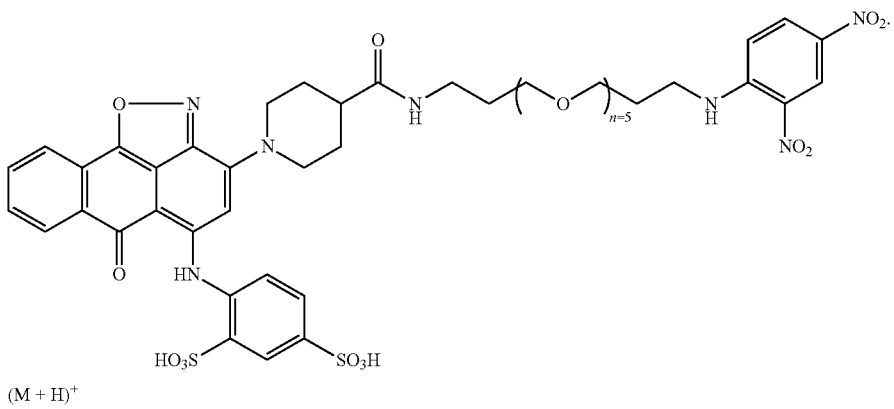

Synthesis of ARM-U2 Derivative 6-ABT-6

ARM-U2 derivative 6-ABT-6 was synthesized as described for 6-ABT-5 only intermediate VIIII (15 mg, 0.027 mmol) was coupled to linker ABT-6 (15.9 mg, 0.027 mmol) as opposed to ABT-1. The product was purified by Gilson C18 reverse phase prep HPLC with a gradient of 25-75% ACN/H2O (both water and ACN contain 0.1% TFA) and following lyophilization yielded 6-ABT-6 in 28% yield (8.0 mg, 0.0076 mmol) as a lyophilized reddish-orange solid. $^1$H NMR (300 MHz, DMSO) δ 11.63-11.76 (m, 1H), 8.88-8.96 (m, 1H), 8.78-8.82 (m, 1H), 8.42-8.49 (m, 1H), 8.18-8.26 (m, 1H), 8.11-8.17 (m, 2H), 7.76-7.86 (m, 2H), 7.66-7.74 (m, 1H), 7.61-7.65 (m, 1H), 7.52-7.58 (m, 1H), 7.17-7.23 (m, 1H), 6.37 (s, 1H), 4.37-4.50 (m, 2H), 3.50 (d, J=3.81 Hz, 24H), 3.02-3.14 (m, 3H), 1.81-1.94 (m, 4H), 1.68-1.80 (m, 2H), 1.58-1.66 (m, 2H). ES-LCMS: m/z 1050.35 (M+H)$^+$.

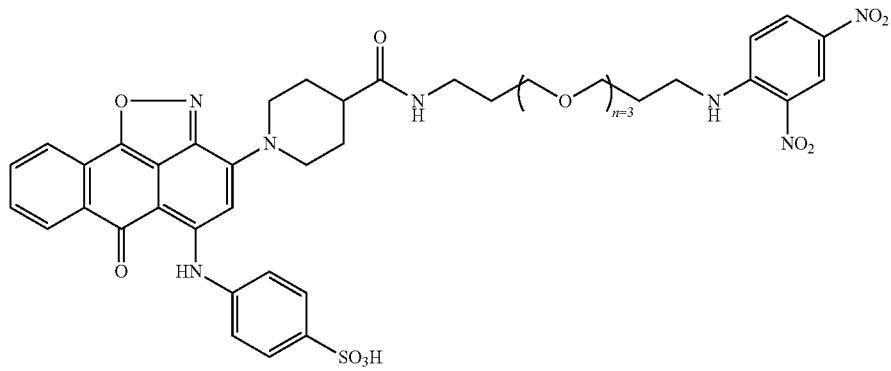

Intermediate X

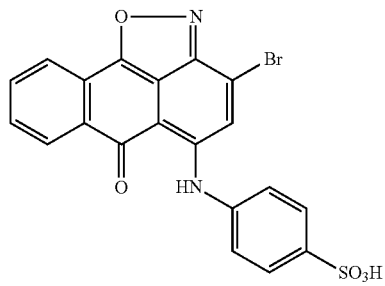

Synthesis of ARM-U2 Derivative 7-ABT-5

To a flame-dried round bottom flask under nitrogen was added di-brorno intermediate II (100 mg, 0.26 mmol), sulfanilic acid (183 mg, 1.1 mmol), and Li2CO3 (146 mg, 1.98 mmol) Anhydrous DMF (5.3 mL) was added and the reaction was heated at 70° C. overnight. The reaction was filtered and purified directly by ISCO reverse-phase chromatography (shielded from direct light) with a gradient of 10-70% ACN/H2O (both water and ACN contain 0.1% TFA). The product containing fractions were pooled and concentrated in vacuo to obtain the pure mono-sulfonated intermediate X isolated in 58% yield (72 mg, 0.153 mmol). Intermediate X (30 mg, 0.06 mmol) was dissolved in anhydrous DMF (400 μL) to which DIPEA (53 μL) and linker ABT-5 (32 mg, 0.06 mmol) were added and the solution allowed to stir at 70° C. overnight. The reaction mixture was purified directly by Gilson C18 reverse phase prep HPLC with a gradient of 30-80% ACN/H2O (both water and ACN contain 0.1% TFA) and following lyophilization yielded 7-ABT-5 in 36% yield (20.7 mg, 0.023 mmol) as a lyophilized reddish-orange solid. ES-LCMS: m/z 888.38 $(M+H)^+$.

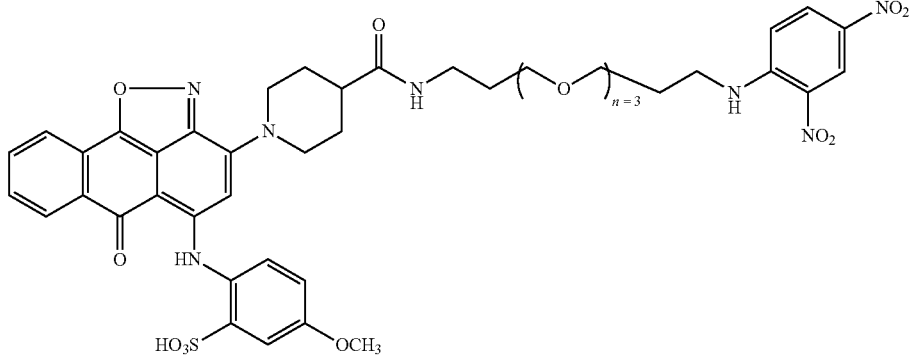

Intermediate XI

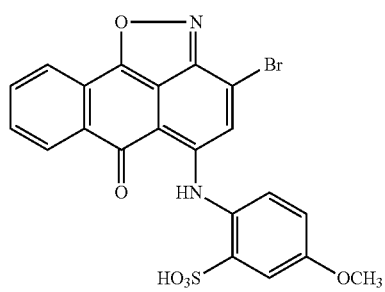

Synthesis of ARM-U2 Derivative 8-ABT-5

ARM-U2 derivative 8-ABT-5 was synthesized in a similar manner to 7-ABT-5 only that 2-amino-5-methoxybenzenesulfonic acid (214 mg, 1.06 mmol) was used in place of sulfanilic acid to obtain pure intermediate XI. Intermediate XI reaction with ABT-5 as above resulted in the isolation of 8-ABT-5 in 32% yield (23.2 mg, 0.025 mmol). ES-LCMS: m/z 918.43 (M+H)$^+$.

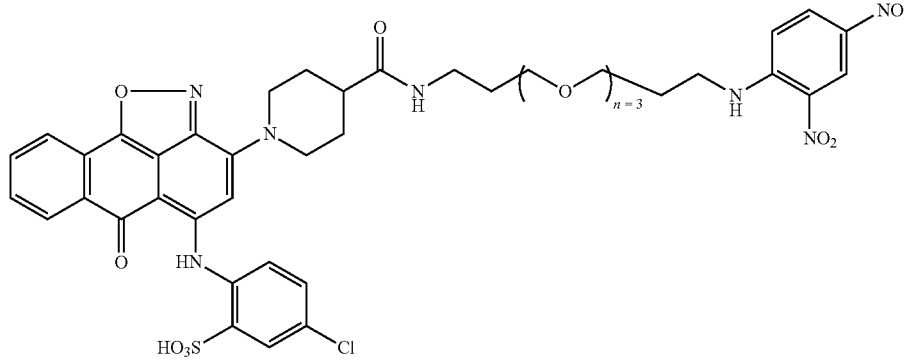

Intermediate XII

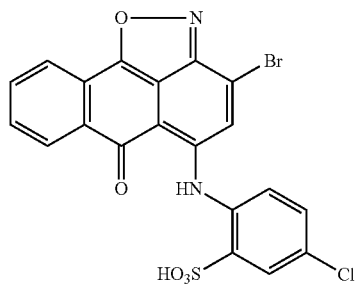

Synthesis of ARM-U2 Derivative 9-ABT-5

ARM-U2 derivative 9-ABT-5 was synthesized in a similar manner to 7-ABT-5 only that 2-amino-5-chlorobenzenesulfonic acid (219 mg, 1.06 mmol) was used in place of sulfanilic acid to obtain pure intermediate XII. Intermediate XII reaction with ABT-5 as above resulted in the isolation of 9-ABT-5 in 75% yield (41.2 mg, 0.045 mmol), ES-LCMS: m/z 922.37 (M+H)$^+$.

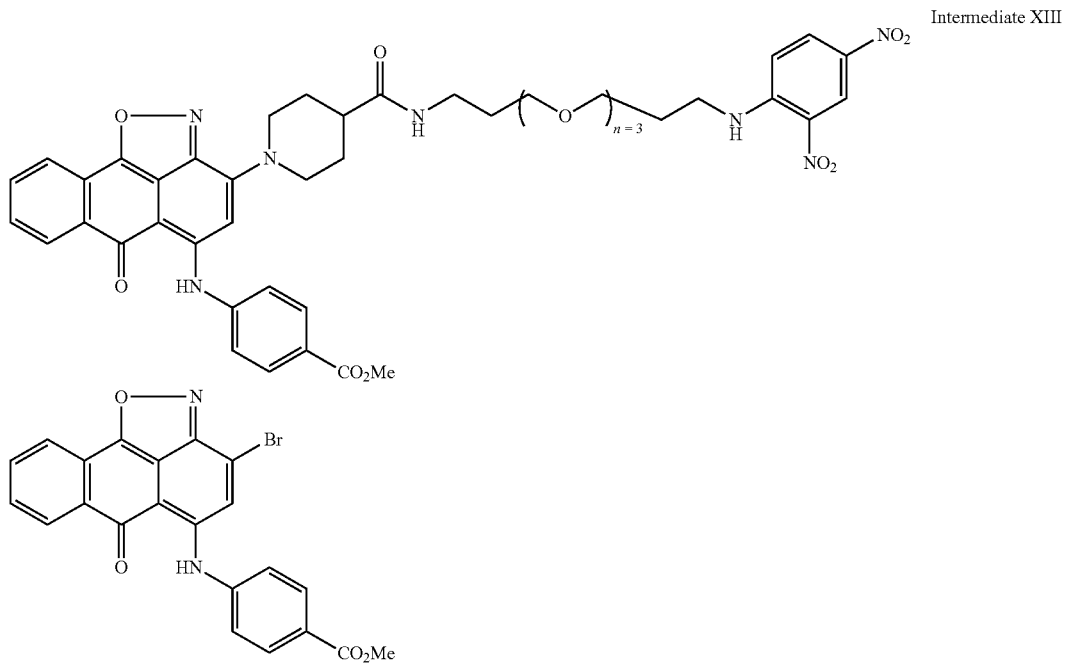

Synthesis of ARM-U2 Derivative 10-ABT-5

Derivative 10-ABT-5 was synthesized as described for 3-ABT-1 only that the di-bromo-isoxazoleinteremidateII was coupled to methyl 4-aminobenzoate in nitrobenzene using AlCl3 to furnish the aniline substituted derivative XIII in 85% yield. Intermediate XIII reaction with ABT-5 as above resulted in the isolation of 10-ABT-5 in 14% yield (53 mg, 0.061 mmol). ES-LCMS: m/z 866.35 (M+H)+.

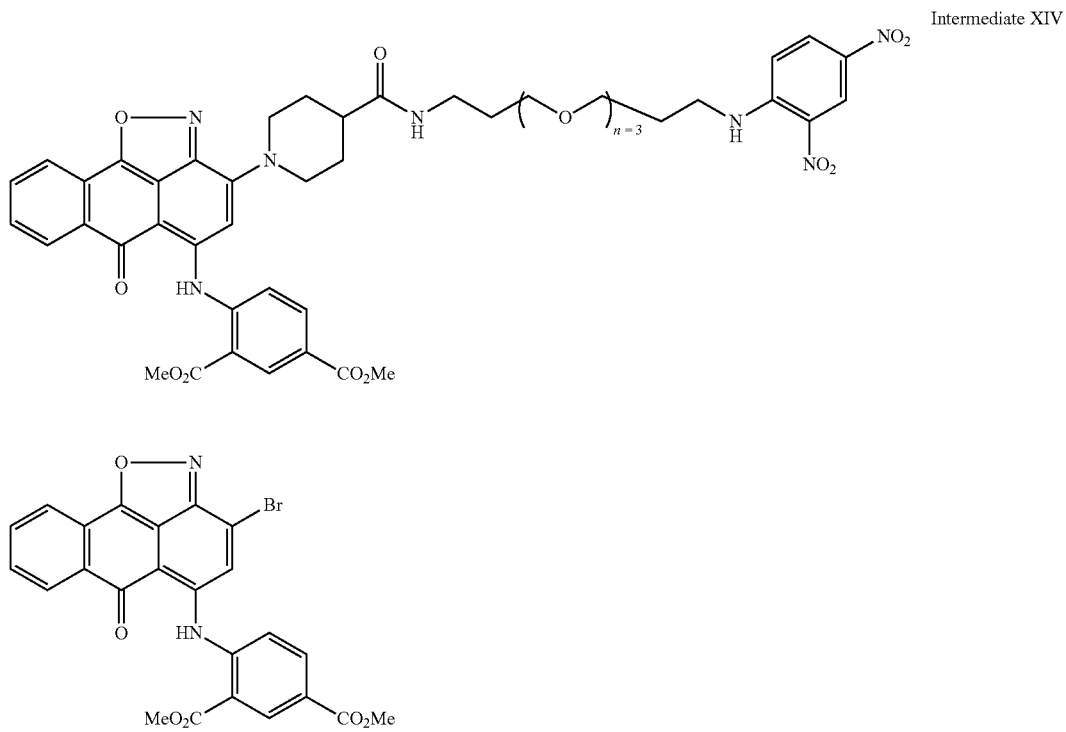

Synthesis of ARM-U2 Derivative 11-ABT-5

Derivative 11-ABT-5 was synthesized as described for 3-ABT-1 only that the di-bromo-isoxazoleinteremidateII was coupled to dimethyl-4-aminoisonphthalate in nitrobenzene using AlCl3 to furnish the aniline substituted derivative XIV in 40% yield. Intermediate XIV reaction with ABT-5 as above resulted in the isolation of 11-ABT-5 in 45% yield (20.6 mg, 0.022 mmol). ES-LCMS: m/z 924.41 (M+H)$^+$.

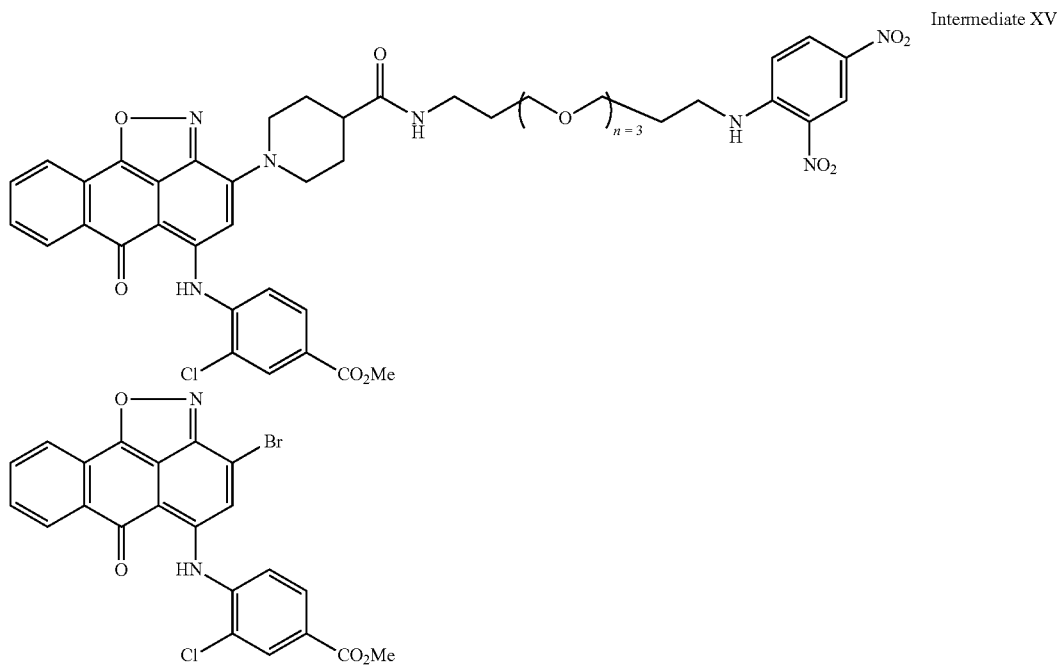

Intermediate XV

Synthesis of ARM-U2 Derivative11-ABT-5

Derivative 12-ABT-5 was synthesized as described for 3-ABT-1 only that the di-bromo-isoxazoleinteremidateII was coupled to methyl 4-amino-3-chlorobenzoate in nitrobenzene using AlCl3 to furnish the aniline substituted derivative XV in 70% yield. Intermediate XV reaction with ABT-5 as above resulted in the isolation of 12-ABT-5 in 64% yield (26.7 mg, 0.030 mmol). ES-LCMS: m/z 900.34 (M+H)$^+$.

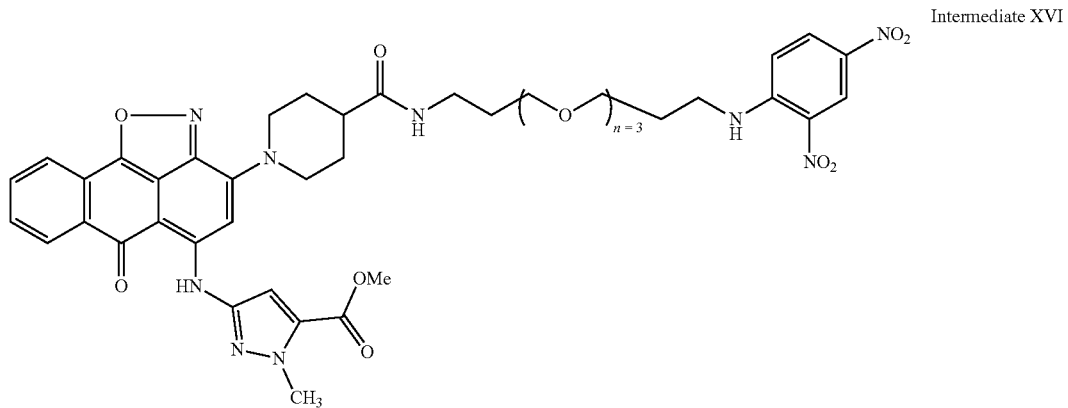

Intermediate XVI

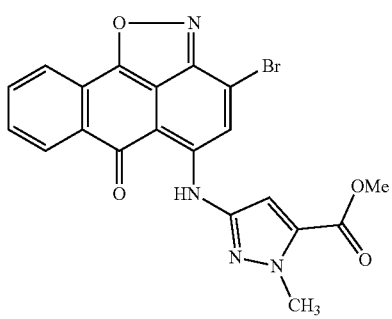

Synthesis of ARM-U2 Derivative 13-ABT-5

Derivative 13-ABT-5 was synthesized as described for 3-ABT-1 only that the di-bromo-isoxazoleinteremidateII was coupled to methyl 3-amino-1-methyl-1H-pyrazole-5-carboxylate in nitrobenzene using AlCl3 to furnish the aniline substituted derivative XVI in 84% yield. Intermediate XVI reaction with ABT-5 as above resulted in the isolation of 13-ABT-5 in 32% yield (15.2 mg, 0.0014 mmol). ES-LCMS: m/z 870.43 (M+H)$^+$.

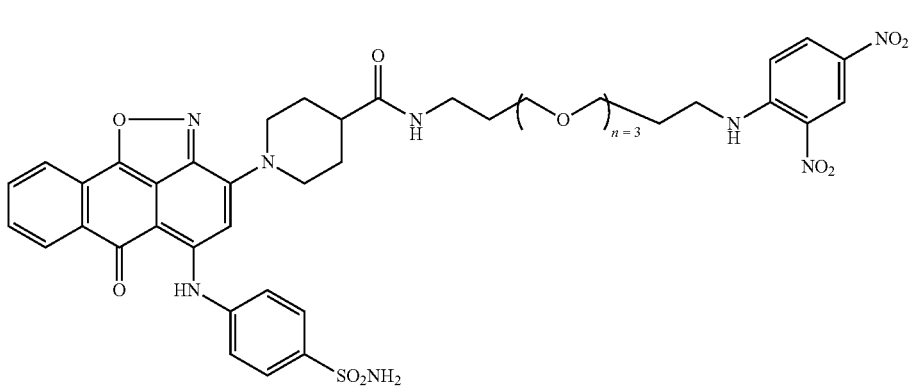

Intermediate XVII

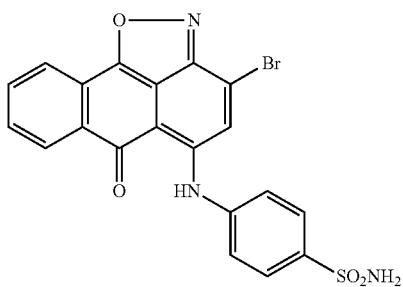

Synthesis of ARM-U2 Derivative 14-ABT-5

Derivative 14-ABT-5 was synthesized as described for 3-ABT4 only that the di-bromo-isoxazoleinteremidateII was coupled to sulfonilamide in nitrobenzene using AlCl3 to furnish the aniline substituted derivative XVII in 76% yield. Intermediate XVII reaction with ABT-5 as above resulted in the isolation of 14-ABT-5 in 62% yield (62 mg, 0.070 mmol). ES-LCMS: m/z 887.43 (M+H)$^+$.

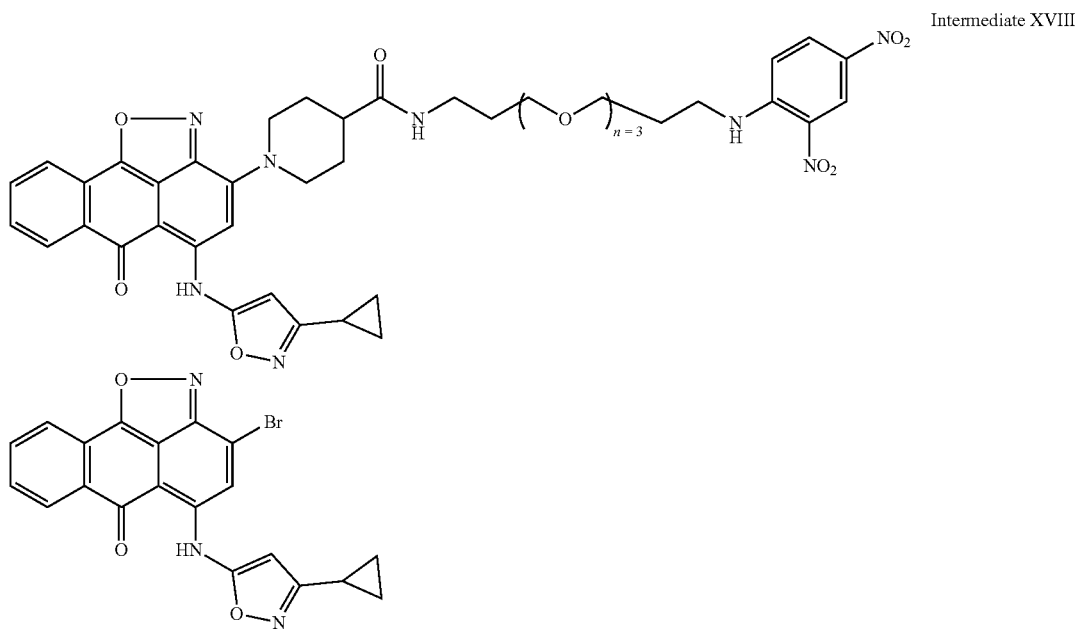

Intermediate XVIII

Synthesis of ARM-U2 Derivative 1.5-ABT-5

ARM-U2 derivative 15-ABT-5 was synthesized in a similar manner to 7-ABT-5 only that 3-cyclopropyl-1,2-oxazol-5-amine was used in place of sulfanilic acid to obtain pure intermediate XVIII. Intermediate XVIII reaction with ABT-5 as above resulted in the isolation of 15-ABT-5 in 7% yield (2.5 mg, 0.003 mmol). ES-LCMS: m/z 839.35 $(M+H)^+$.

Synthesis of ARM-U2 Derivative 16-ABT-5

ARM-U2 derivative 16-ABT-5 was synthesized in a similar manner to 7-ABT-5 only that ethyl 3-aimno-1-methyl-1H-pyrazole-4-carboxylate was used in place of sulfanilic acid to obtain pure intermediate XIX. Intermediate XIX reaction with ABT-5 as above resulted in the isolation of 16-ABT-5 in 23% yield (4.3 mg, 0.005 mmol). ES-LCMS; m/z 884.37 $(M+H)^+$.

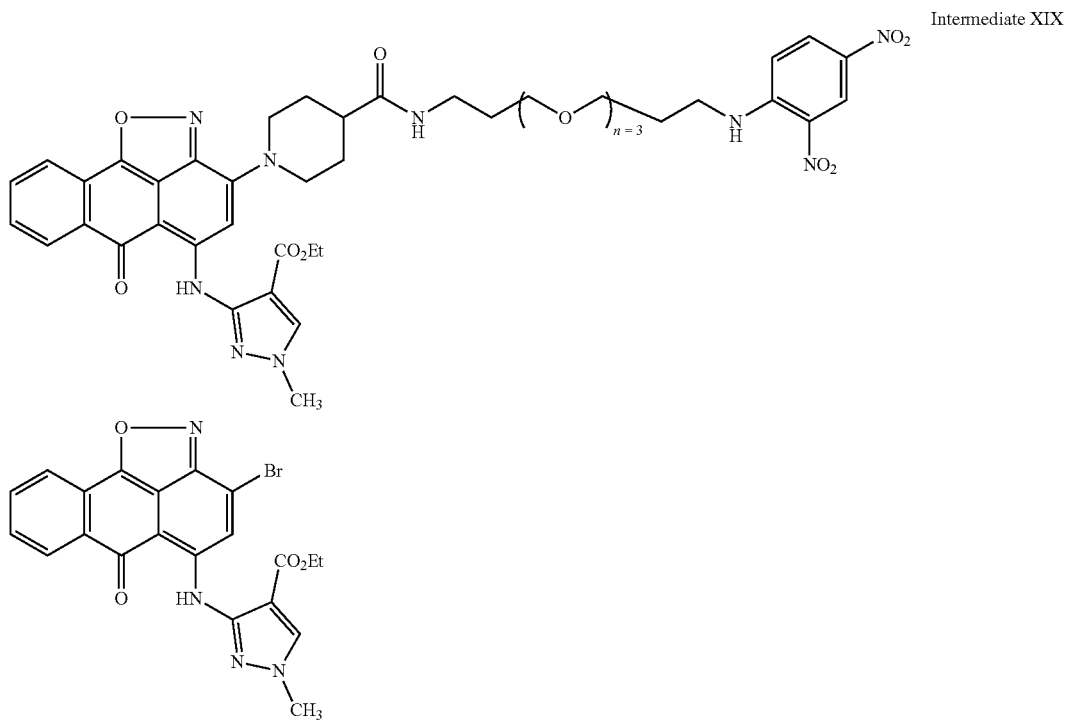

Intermediate XIX

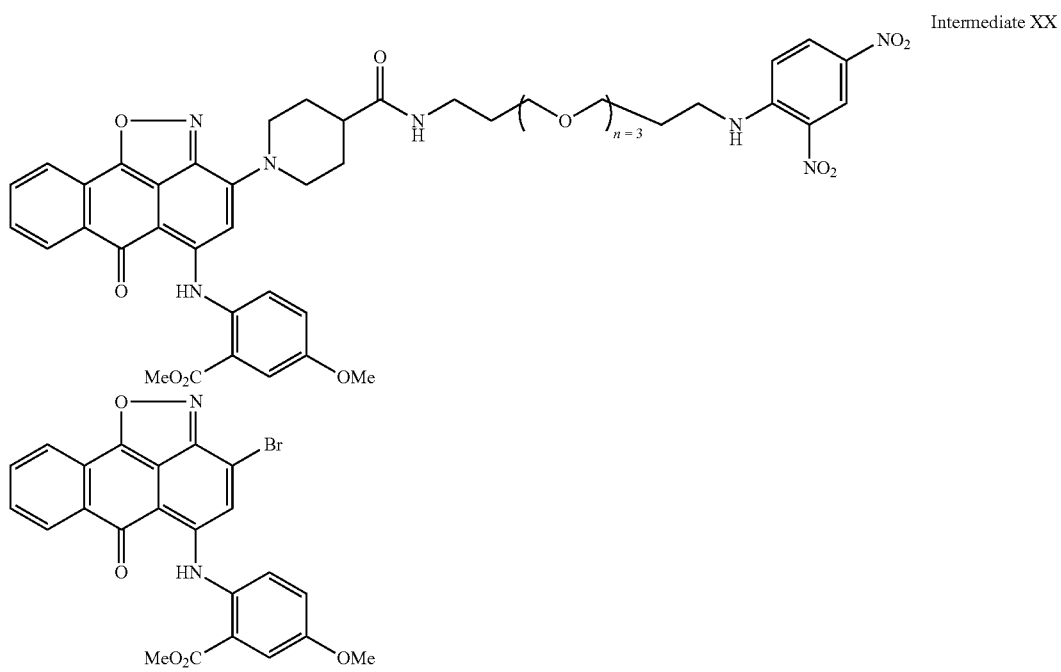

Intermediate XX

Synthesis of ARM-U2 Derivative 17-ABT-5

ARM-U2 derivative 16-ABT-5 was synthesized in a similar manner to 7-ABT-5 only that methyl 2-amino-5-methyoxybenzoate was used in place of sulfanilic acid to obtain pure intermediate XX. Intermediate XX reaction with ABT-5 as above resulted in the isolation of 17-ABT-5 in 53% yield (10 mg, 0.011 mmol). ES-LCMS: m/z 896.54 (M+H)$^+$.

Synthesis of ARM-U2 Derivative 18-ABT-5

ARM-U2 derivative 18-ABT-5 was synthesized in a similar manner to 7-ABT-5 only that 2-amino-5-chlorobenzoic acid was used in place of sulfanilic acid to obtain pure intermediate XXI. Intermediate XXI reaction with ABT-5 as above resulted in the isolation of 18-ABT-5 in 44% yield (16 mg, 0.018 mmol). ES-LCMS: m/z 886.41 (M+H)$^+$.

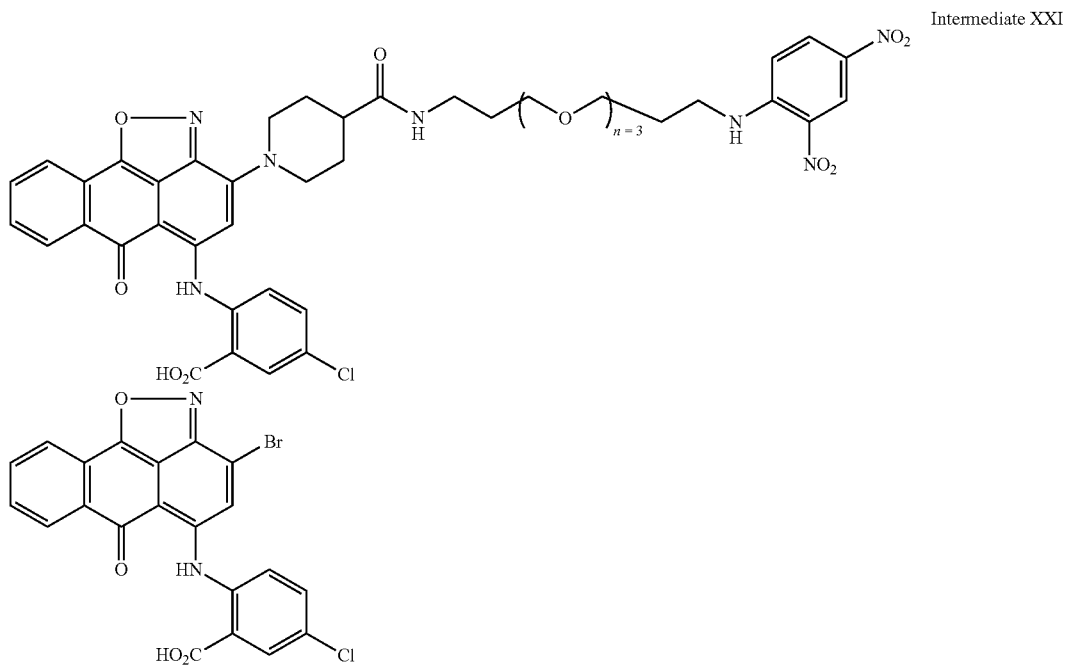

Intermediate XXI

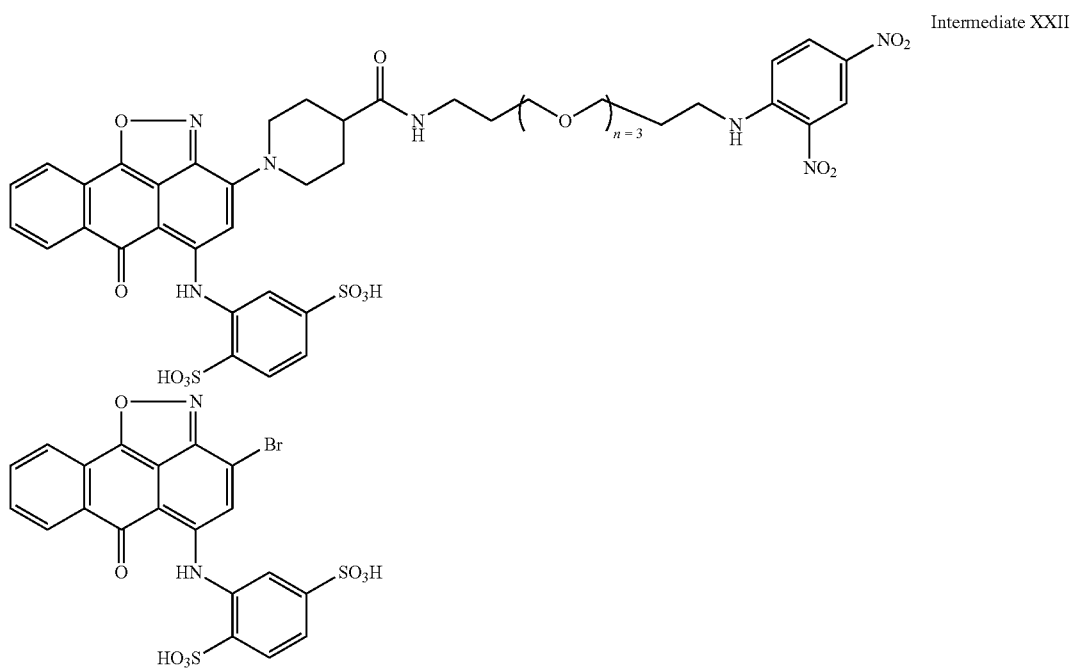

Intermediate XXII

Synthesis of ARM-U2 Derivative 19-ABT-5

ARM-U2 derivative 19-ABT-5 was synthesized in a similar manner to 7-ABT-5 only that 2-amino-1,4-benzenedisulfonic acid was used in place of sulfanilic acid to obtain pure intermediate XXII. Intermediate XXII reaction with ABT-5 as above resulted in the isolation of 19-ABT-5 in 90% yield (15.8 mg, 0.016 mmol). ES-LCMS: 968.47 (M+H)$^+$.

Biological Testing

Biology reagents: A172 human glioblastoma cells are purchased from ATCC (# CRL-1620), grown in T-flasks with Dulbecco's modified Eagle's medium supplemented with 10% HI-FBS, and detached by the EDTA detachment procedure. U937 Cells are purchased from ATCC (# CRL-1593.2), grown in Petri dishes as a suspension with RPMI-1640 medium supplemented with 10% HI-FBS and 1% penicillin-streptomycin. All cell culturing is done using colored ADCP Media RPMI Medium 1640, liquid Invitrogen #11875-093 supplemented with 10% HI-FBS and 1% penicillin-streptomycin. Anti-dinitrophenyl-KLH Rabbit IgG Fraction with and without biotin were purchased from Invitrogen # A6430 (Lot 807872) as a solution and stored at 4° C. Human uPAR Antibody: Polyclonal goat IgG R&D Systems # AF807 was purchased as a lyophilized solid and was stored at −20° C., as a solution in 250 µL of sterile DPBS. Human urokinase, isolated from human urine was purchased from PROSPEC as a lyophilized white solid and reconstituted at a concentration of 1 mg/mL (approx. 18.5 µM) in milliQ water and stored at −20° C. Recombinant human uPAR with carrier protein was obtained as a white lyophilized solid from R&D systems and dissolved in DPBS at a concentration of 100 ug/mL. (approx. 2 uM) and stored at −20° C.

Competitive ELISA uPAR Binding Assays

The affinity of derivatives are assayed using a competitive ELISA binding assay. The assay involves the immobilization of urokinase, a natural high affinity ligand for uPAR followed by the addition of a fixed concentration of recombinant uPAR protein and increasing concentrations of test compounds which competes with urokinase for binding to the uPA binding site of uPAR. Following several washing steps, the amount of uPAR bound is quantified by a biotinylated anti-uPAR antibody and avidin-HRP and can be fit to a competitive binding model allowing for determination of the uPAR/test compound $K_d$.

Antibody Recruiting Cellular Assays

The derivatives of the present invention are expected to recruit ami-DNP antibodies to the surface of A-172 and B-16 cancer cells over-expressing uPAR. These assays involve the incubation of derivatives with target cancer cells followed by the addition of biotinylated anti-DNP antibodies and streptavidin-AlexaFluor conjugates. After several washing steps, the amount of compound bound simultaneously to both the cell surface and anti-DNP antibodies was detected using flow cytometry by observing shifts in FL-2 and FL-3 fluorescence. These experiments can also be conducted on both B16+uPAR cell lines and B16-uPAR cell lines in addition to studies on A172 cells in the presence and absence of exogenously added competitor uPAR to assess selective binding to the cell surface via cell surface uPAR.

Fluorescence and ELISA Binding Studies

Selected derivatives were assayed for their ability to bind recombinant uPAR using a fluorescence quenching assay. The compounds stored at −20° C. as DMSO stocks were diluted into PBS aliquots at a fixed 50 nM concentration. Increasing concentrations of recombinant uPAR were mixed with each compound containing aliquot and the fluorescence of the solution measured following 1 h equilibration times. Increasing concentrations of uPAR resulted in saturable quenching of intrinsic fluorescence generating a binding isotherm to extract the equilibrium dissociation constant for binding to uPAR. To confirm that the observation of uPAR dependent fluorescence quenching was indeed due to specific binding to uPAR and to validate binding to uPAR specifically via the uPA binding site, a direct binding ELISA assay was developed. In this assay, clear 96-well high-binding plates from CoStar, were loaded with 100 μl/well of 50 nM recombinant uPAR 807-UK-100-CF from R&D systems prepared from a 100 μg/ml (approx. 2.1 μM) stock of uPAR in PBS and left overnight at room temperature to equilibrate. Following equilibration, the plate was washed with wash buffer 1× (400 μl/well of 0.05% Tween/PBS), blotted dry and blocked for 1 hr with 300 uL/well of 2% BSA/PBS. Following blocking, the plate was washed with 400 μl of the wash buffer and blotted dry. Dilutions of each derivative from 100× stocks in DMSO were made into 100 μL/WELL of 1% BSA/PBS and left to equilibrate with immobilized uPAR fbr 2 h at RT. Following the binding step, the plate was washed 1×200 μl and 1×400 μl of wash buffer and blotted dry. A solution of anti-DNP rabbit IgG KLH biotinylated antibody was prepared in 1% BSA/PBS from a 10,000× commercially available stock of 2 mg/ml in 500 μl (Life Technologies) and added in a volume of 100 μl/well, left to equilibrate for 1 h at RT. To assess selectivity of binding of test compounds to the uPA binding site of uPAR, 100 nM competitor uPA-ATF (Innovative Research), the amino terminal fragment of uPA which retains the complete binding capability of urokinase for uPAR, was added during the biotinylated anti-DNP antibody incubation step. Following incubation with the antibody, the plate was washed 1×200 μl 1×400 μl of wash buffer and blotted dry. A solution of avidin-HRP was prepared by diluting 20 μl of stock solution (e-bioscience) into 10 ml of 1% BSA/PBS solution and 100 μl added to each well and incubated for 20 min at RT. Following 3×400 ul washes and blotting, 100 ul of HRP substrate solution (TMB-substrate, Thermo) was added and the wells allowed to develop until a clear difference between negative control (no uPAR loaded) and wells containing test compounds could be observed by differences in the emergence of blue color at which time the development was halted by the addition of 50 μl 4N sulfuric acid. The absorbance at 450 nm was measured using an in-house Perkin-Elmer fluorescence plate reader.

All derivatives were assessed for their ability to hind selectively to recombinant uPAR in vitro using a competitive ELISA binding assay. DMSO stock solutions of each derivative stored at −20° C. were titrated into wells pre-coated with human urokinase (isolated from human urine, ProSpec 1 mg/mL deionized water 18.5 μM) in the presence of uPAR. Selective binding to uPAR by compounds at the uPA binding site competes with uPAR-uPA binding which is required for a positive UV 450 nm absorbance signal. Increasing concentrations of test compound displace increasing amounts of uPAR from uPA which is detected by anti-uPAR/biotin labeled antibodies followed by avidin-HRP.

Antibody Recruiting Assays

A172 glioblastoma cells (ATCC, CRL-1620) were suspended in Assay Media (phenol-free RPMI 1640 medium plus 10% ultra-low IgG PBS). $10^5$ cells taken up in 50 μL media or media containing exogenous uPAR were mixed with a fixed concentration of the indicated compound from 100×DMSO stocks. After a 1 hour incubation on ice, cells were washed with 1.5 mL of cold Assay Media, pelleted for 2 min at 200 rcf, aspirated, and resuspended in 100 L of fresh assay media with 133 nM of anti-DNP-biotin-xx conjugate antibody (Invitrogen). After 15 min more on ice, cells were washed 2× with 1.5 mL of cold Assay Media before flow cytometric analysis. Propidium iodide was added from a 1000× stock as a cell viability stain (FL-3 positive) and antibody recruiting to the cell surface was evaluated by measuring increasing cell counts in the FL-4 channel negative for FL-3 (lower right quadrant of representative dot plots). The evaluation of selective binding to uPAR was carried out by performing the antibody recruiting assay described above identically, save that B16-F10 melanoma cells, either stably transfected with human uPAR or the empty vector pc DNA3.1 (isogenic negative control), were used in place of A172 cells.

Compound Testing

ELISA assay substantially as described above was used to test certain of the compounds of the present invention for biological characteristics. In addition, the compound 6-ABT-1 as described in WO2017/023994 was tested as a control. Results from the biological testing are shown in Table A, below.

TABLE A

| Compound | IC50 (μM) | Ki | Ratio of IC50 (Compound)/ IC50 6-ABT-1 |
| --- | --- | --- | --- |
| ARM-U2 derivative 6-ABT-5 | 0.5436 | 11 | 0.7 |
| ARM-U2 derivative 6-ABT-6 | 1.356 | 27.8 | 1.6 |
| ARM-U2 derivative 7-ABT-5 | 2.36 | 48.41 | 1.15 |
| ARM-U2 derivative 8-ABT-5 | 0.54 | 10.95 | 0.28 |
| ARM-U2 derivative 9-ABT-5 | 0.485 | 9.84 | 0.255 |
| ARM-U2 derivative 10-ABT-5 | >100 | >2000 | 71.4 |
| ARM-U2 derivative 11-ABT-5 | >100 | >2000 | >56 |
| ARM-U2 derivative 12-ABT-5 | >100 | >2000 | 71.4 |
| ARM-U2 derivative 13-ABT-5 | >100 | >2000 | 71.4 |
| ARM-U2 derivative 14-ABT-5 | >100 | >2000 | 71.4 |
| ARM-U2 derivative 15-ABT-5 | 18 | 371.0 | 12.85 |
| ARM-U2 derivative 16-ABT-5 | 55.22 | 1138.6 | 39.41 |
| ARM-U2 derivative 17-ABT-5 | >100 | >2000 | >31 |
| ARM-U2 derivative 18-ABT-5 | 3.088 | 63.5 | 0.98 |
| ARM-U2 derivative 19-ABT-5 | 2.566 | 52.7 | 0.81 |

Throughout this application, various publications are referenced by author name and date, or by patent number or patent publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

Those skilled in the art will recognize, or be able to ascertain using no more than routine experimentation, numerous equivalents to the specific procedures described herein. Such equivalents are considered to be within the, scope of this invention and are covered by the following claims. Furthermore, it is intended that specific items within lists of items, or subset groups of items within larger groups of items, can be combined with other specific items, subset groups of items or larger groups of items whether or not there is a specific disclosure herein identifying such a combination.

The invention claimed is:
1. A compound according to the general structure:

TBT-LINKER-ABT

Where ABT is an antibody binding moiety comprising a hapten which is capable of binding to an antibody in said patient or subject, wherein ABT is a group according to the chemical formula:

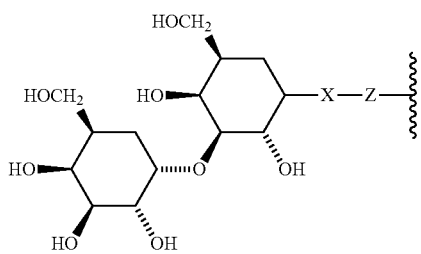

where X is CH$_2$, O, N—R$^{1'}$, or S;
R$^{1'}$ is H or C$_1$-C$_3$ alkyl; and
Z is a bond, a monosaccharide, disaccharide or oligosaccharide, or
ABT is a group according to the chemical formula:

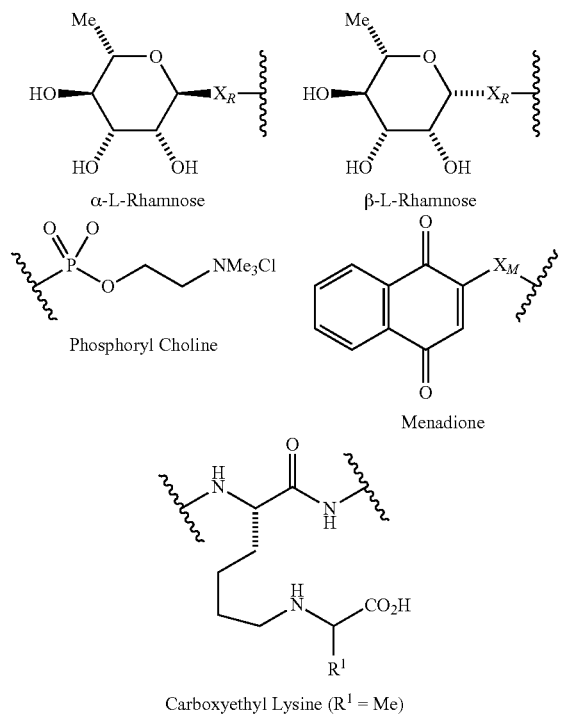

α-L-Rhamnose    β-L-Rhamnose

Phosphoryl Choline    Menadione

Carboxyethyl Lysine (R$^1$ = Me)

where X$_R$ is O, S or NR$^1$; and
X$_M$ is O, NR$^1$ or S, and
R$^1$ is H or a C$_1$-C$_3$ alkyl group, or
ABT is a group according to the chemical formula:

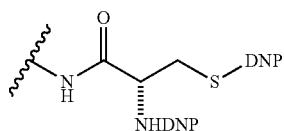

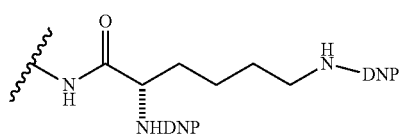

or a group according to the chemical formula:

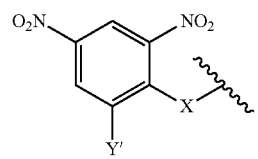

where Y' is H or NO$_2$;
X is O, CH$_2$, NR$^1$, S(O), S(O)$_2$, —S(O)$_2$O, —OS(O)$_2$, or OS(O)$_2$O; and
R$^1$ is H, a C$_1$-C$_3$ alkyl group, or a —C(O)(C$_1$-C$_3$) group, or
ABT is a group according to the chemical formula:

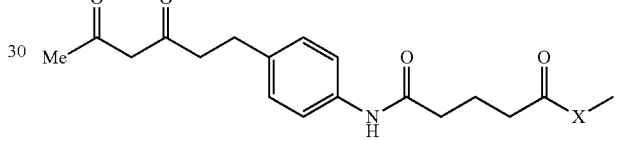

where X" is O, CH$_2$, NR$^1$, S; and
R$^1$ is H, a C$_1$-C$_3$ alkyl group or a —C(O)(C$_1$-C$_3$) group; or

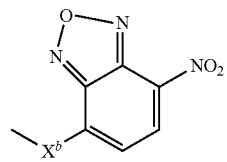

where X$^b$ is a bond, O, CH$_2$ or NR$^1$ or S; and
R$^1$ is the same as above; or
ABT is a group according to the chemical structure:

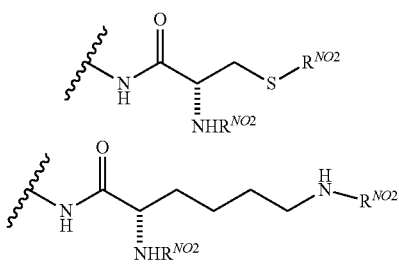

where R$^{NO2}$ is a dinitrompthenyl group optionally linked through CH$_2$, S(O), S(O)$_2$, —S(O)$_2$O, —OS(O)$_2$, or OS(O)$_2$O; or a dinitrophenyl group according to the chemical structure:

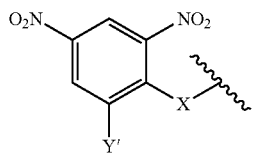

where Y' is H or $NO_2$;
X is O, $CH_2$, $NR^1$, S(O), $S(O)_2$, —$S(O)_2O$, —$OS(O)_2$, or $OS(O)_2O$; and
$R^1$ is H, a $C_1$-$C_3$ alkyl group, or a —$C(O)(C_1$-$C_3)$ group;
CT is a group according to the chemical formula:

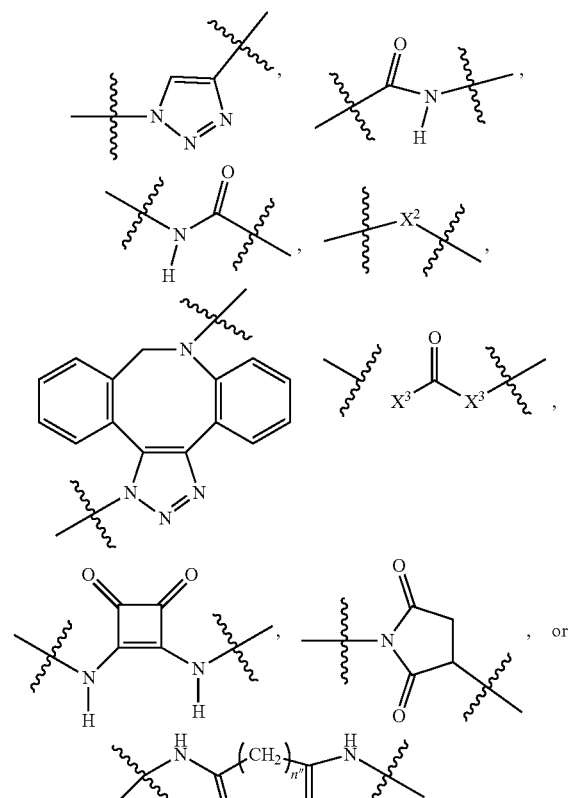

where $X^2$ is $CH_2$, O, S, $NR^4$, S(O), $S(O)_2$, —$S(O)_2O$, —$OS(O)_2$, or $OS(O)_2O$;
$X^3$ is O, S, $NR^4$;
$R^4$ is H, a $C_1$-$C_3$ alkyl or alkanol group, or a —$C(O)(C_1$-$C_3)$ group; and
n" is independently 0 to 8:
LINKER is a linker molecule which chemically links through covalent bonding TBT to ABT, optionally through a CT group, wherein said linker molecule is a group according to the chemical structure:

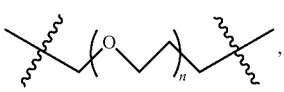

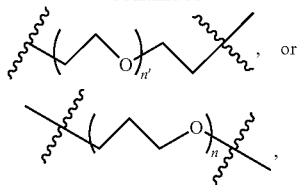

or
a group according to the chemical structure:

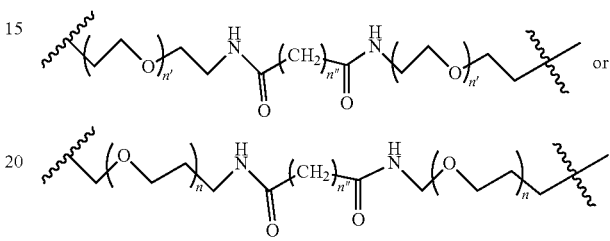

where each n and n' is independently 1 to 25;
each n" is independently 0 to 8, or
LINKER is a group according to the chemical structure:

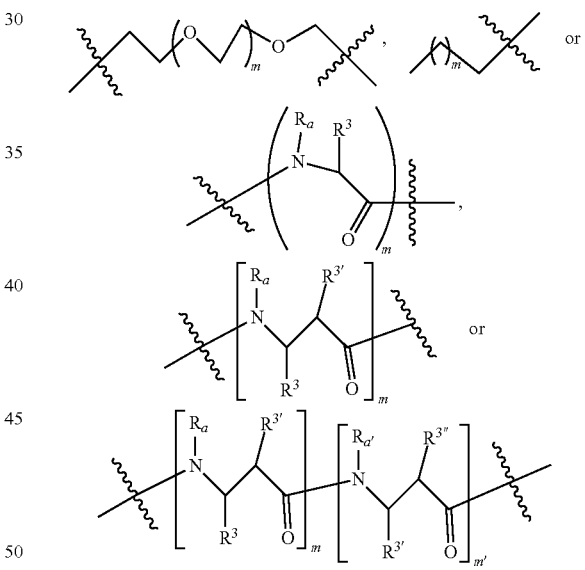

where $R_a$ and $R_{a'}$ are each independently H, $C_1$-$C_3$ alkyl, alkanol, aryl or benzyl, or $R_a$ and $R^3$ or $R_{a'}$ and $R^{3'}$ together form a pyrroline or hydroxypyrrolidine ring with the nitrogen atom attached to $R_a$ or $R_{a'}$, respectively or $R^3$ and $R^{3'}$ and $R^{3''}$ are each independently a side chain of a natural or unnatural amino acid (D- or L-) wherein said amino acid is selected from the group consisting of alanine wherein said sidechain is methyl, arginine wherein said sidechain is propyleneguanidine, asparagine wherein said sidechain is methylenecarboxyamide, aspartic acid wherein said sidechain is ethanoic acid, cysteine wherein said sidechain is thiol or di-thiol, glutamine wherein said sidechain is ethylcarboxyamide, glutamic acid wherein said sidechain is propanoic acid, histidine wherein said sidechain is methyleneimidazole, isoleucine wherein said sidechain is 1-methylpropane, leucine wherein said sidechain is 2-methylpropane, lysine wherein said sidechain is butyleneamine, methionine wherein said sidechain is ethylmethylthioether, phenylalanine wherein said sidechain is benzyl, serine wherein said sidechain is methanol, threonine wherein said sidechain is 1-hydroxyethane, tryptophan wherein said sidechain is methyleneindole, tyrosine wherein said sidechain is methylene phenol or valine wherein said sidechain is isopropyl; and m and m' are each independently an integer from 1 to 100, or LINKER is a group according to the chemical formula:

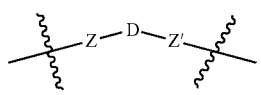

where Z and Z' are each independently a bond, —$(CH_2)_i$—O, —$(CH_2)_i$—S, —$(CH_2)_i$—N—R,

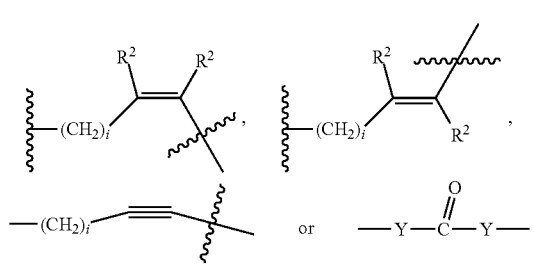

wherein said —$(CH_2)_i$ group, if present in Z or Z', is bonded to a connector group (CT), ABT and/or TBT;

Each R is H, or a $C_1$-$C_3$ alkyl or alkanol group;
Each $R^2$ is independently H or a $C_1$-$C_3$ alkyl group;
Each Y is independently a bond, O, S or N—R;
Each i is independently 0 to 100;
D is

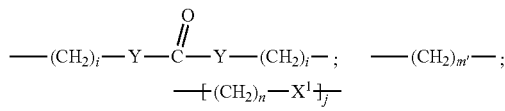

or
a bond, with the proviso that Z, Z' and D are not each simultaneously bonds;
j is 1 to 100;
m' is 1 to 100;
n is 1 to 100;
$X^1$ is O, S or N—R; and
R is as described above;

LINKER-ABT is a chemical moiety wherein said linker molecule LINKER is covalently bonded to ABT;

TBT is a moiety which binds to an active site of urokinase-type plasminogen activator receptor (uPAR) on the surface of cancer cells of a patient or subject and to said LINKER-ABT group at the amide amine of said TBT moiety, selected from a moiety according to the chemical formula:

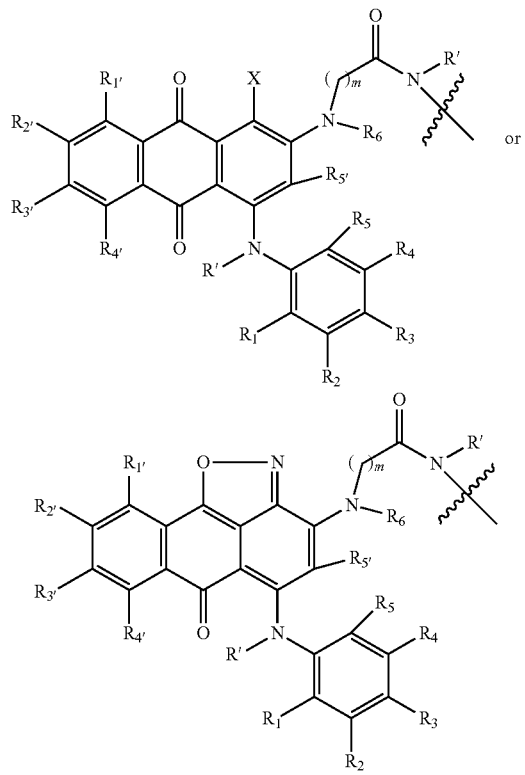

wherein X=H, F, Cl, Br, $CF_3$, $MeSO_2$, $CH_3O$, $CF_3O$ $N(R^N)_2$, where each $R^N$ is independently H or a $C_1$-$C_3$ alkyl group;

$R_1$, $R_2$, $R_3$, $R_4$ and $R_5$ are each independently H, a halogen, a $C_1$-$C_3$ alkyl group optionally substituted with one or two hydroxyl groups or up to three fluoro groups, $NO_2$, CN, a $(CH_2)_m OR^E$ (O-alkyl) group, a $(CH_2)_m COR^E$ (keto) group, a $(CH_2)_m COOR^E$ (carboxy ester) group, a $(CH_2)_m SO_3H$ group, a $(CH_2)_m OCOR^E$ (oxycarbonyl ester) group,

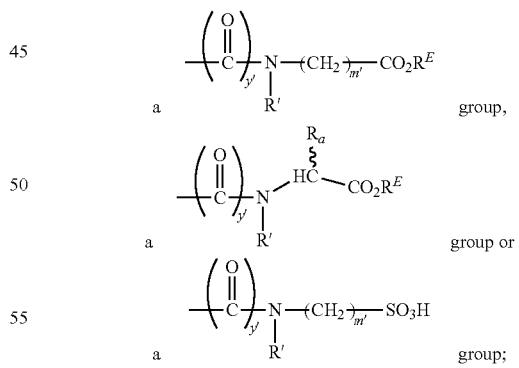

Each $R^1$ is independently H or a $C_1$-$C_3$ alkyl group;
$R_a$ is a sidechain derived from a natural or unnatural amino acid (D- or L-) wherein said amino acid is selected from the group consisting of alanine wherein said sidechain is methyl, arginine wherein said sidechain is propyleneguanidine, asparagine wherein said sidechain is methylenecarboxyamide, aspartic acid wherein said sidechain is ethanoic acid, cysteine wherein said sidechain is thiol or di-thiol, glutamine (wherein said sidechain is ethylcarboxyamide, glutamic acid wherein said sidechain is propanoic acid, histidine wherein said sidechain is methyleneimidazole, isoleucine wherein said sidechain is 1-methylpropane, leucine wherein said sidechain is 2-methylpropane, lysine wherein said sidechain is butyleneamine, methionine wherein said sidechain is ethylmethylthioether, phenylalanine wherein said sidechain is benzyl, proline wherein said sidechain $R_a$ forms a cyclic ring with R' and the adjacent nitrogen group to form a pyrrolidine group, hydroxyproline wherein said sidechain $R_a$ forms a cyclic ring with R' and the adjacent nitrogen group to form a hydroxypyrrolidine group, serine wherein said sidechain is methanol, threonine wherein said sidechain is 1-hydroxyethane, tryptophan wherein said sidechain is methyleneindole, tyrosine wherein said sidechain is methylene phenol or valine wherein said sidechain is isopropyl;

Each $R^E$ is H or a $C_1$-$C_6$ alkyl group optionally substituted with one or two hydroxyl groups or up to three chloro or fluoro groups;

$R_{1'}$, $R_{2'}$, $R_{3'}$, $R_{4'}$ and $R_{5'}$ are each independently H, a halogen, a
  $C_1$-$C_6$ alkyl group optionally substituted with one or two hydroxyl groups or up to three chloro or fluoro groups, $NO_2$, CN, a $(CH_2)_m OR^E$ (O-alkyl) group, a $(CH_2)_m COOR^E$ (carboxy ester) group, a $(CH_2)_{m'}$—O—$COR^E$ (oxycarbonyl ester) group or a $(CH_2)_{m'} COR^E$ (keto) group;

$R_1$ is H or $SO_3H$, $R_2$ is H, $CO_2H$, $SO_3H$, —$NHCH_2$—$CO_2H$, —$NHCH_2$—$SO_3H$, —C(O)—$NHCH_2$—$CO_2H$ or —C(O)—$NHCH_2$—$SO_3H$, $R_3$ is H, $CO_2H$, or $SO_3H$, $R_4$ is H, $CO_2H$, or $SO_3H$, and $R_5$ is H, $CO_2H$, or $SO_3H$;

Each m' is independently 0, 1, 2, 3, 4, 5, or 6;
Each y' is independently 0, 1 or 2;
m=0-5, and
$R_6$=H or $C_1$-$C_4$ lower alkyl;
or a pharmaceutically acceptable salt, stereoisomer or enantiomer thereof.

2. A compound according to claim 1 wherein said LINKER-ABT moiety is selected from the group consisting of:

where $X_L$ is $N(R^1)$, O, S, S(O), $SO_2$, $S(O)_2O$, —$OS(O)_2$, or $OS(O)_2O$;
$R^1$ is H, a $C_1$-$C_3$ alkyl group or a —$C(O)(C_1$-$C_3)$ group;
each n and n' is independently 1 to 25; and
each n" is independently 0 to 8.

3. A compound according to claim 1 wherein LINKER is a linker group according to the chemical structure:

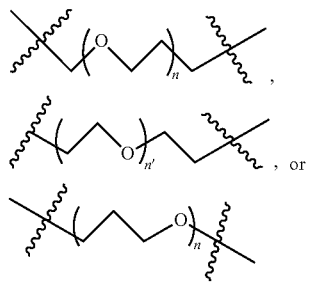

where each n and n' is independently 1 to 25; and
each n" is independently 0 to 8.

4. A compound according to claim 1 wherein LINKER is a group according to the chemical structure:

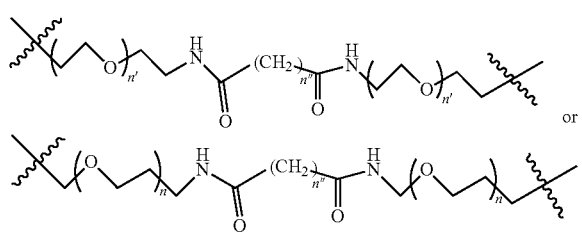

where each n and n' is independently 1 to 25;
each n" is independently 0 to 8;
where n is about 1 to 100; or

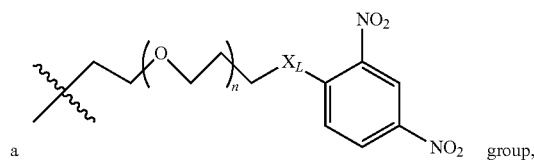

a

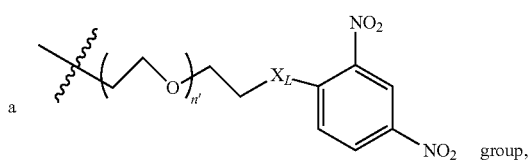

a

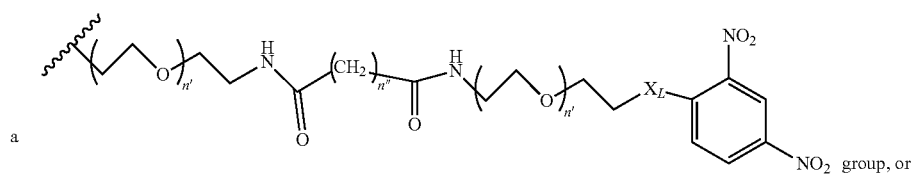

a

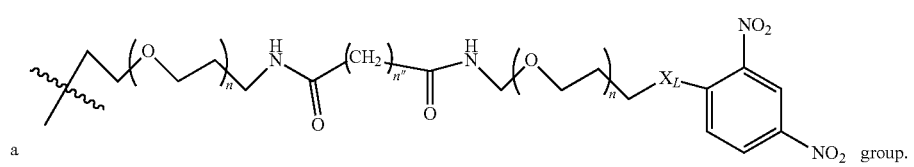

a

LINKER is a group according to the chemical structure:

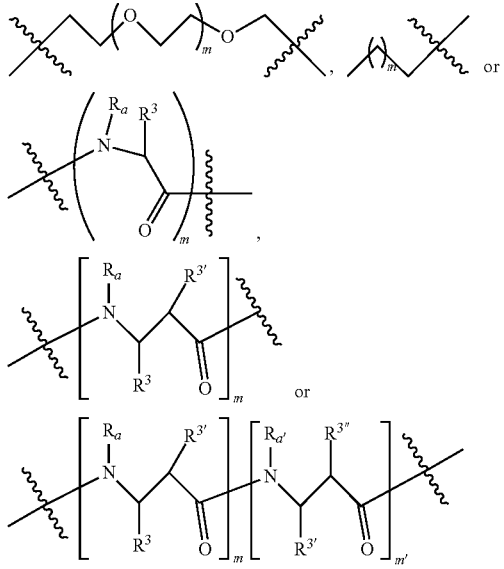

where $R_a$ and $R_{a'}$ are each independently H, $C_1$-$C_3$ alkyl, alkanol, aryl or benzyl, or $R_a$ and $R^3$ or $R_{a'}$ and $R^{3'}$ together form a pyrroline or hydroxypyrrolidine ring with the nitrogen atom attached to $R_a$ or $R_{a''}$ respectively or $R^3$ and $R^{3'}$ and $R^{3''}$ are each independently a side chain of a natural or unnatural amino acid (D- or L-) wherein said amino acid is selected from the group consisting of alanine wherein said sidechain is methyl, arginine wherein said sidechain is propyleneguanidine, asparagine wherein said sidechain is methylenecarboxyamide, aspartic acid wherein said sidechain is ethanoic acid, cysteine wherein said sidechain is thiol or di-thiol, glutamine wherein said sidechain is ethylcarboxyamide, glutamic acid wherein said sidechain is propanoic acid, histidine wherein said sidechain is methyleneimidazole, isoleucine wherein said sidechain is 1-methylpropane, leucine wherein said sidechain is 2-methylpropane, lysine wherein said sidechain is butyleneamine, methionine wherein said sidechain is ethylmethylthioether, phenylalanine wherein said sidechain is benzyl, serine wherein said sidechain is methanol, threonine wherein said sidechain is 1-hydroxyethane, tryptophan wherein said sidechain is methyleneindole, tyrosine wherein said sidechain is methylene phenol or valine wherein said sidechain is isopropyl; and m and m' is each independently an integer from 1 to 100.

5. A compound according to claim 1 wherein LINKER is a group according to the chemical formula:

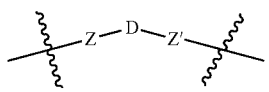

where Z and Z' are each independently a bond, —$(CH_2)_i$—O, —$(CH_2)_i$—S, —$(CH_2)_i$—N—R,

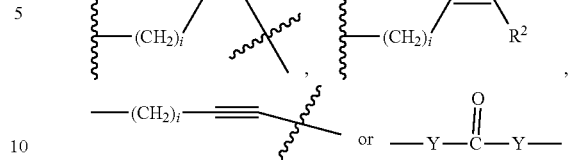

wherein said —$(CH_2)_i$ group, if present in Z or Z', is bonded to a connector (CT), ABT and/or TBT;
Each R is H, or a $C_1$-$C_3$ alkyl or alkanol group;
Each $R^2$ is independently 1-I or a $C_1$-$C_3$ alkyl group;
Each Y is independently a bond, O, S or N—R;
Each i is independently 0 to 100;
D is

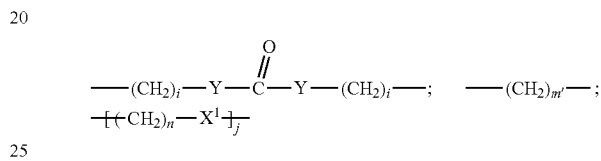

or
a bond, with the proviso that Z, Z' and D are not each simultaneously bonds;
j is 1 to 100;
m' is 1 to 100;
n is 1 to 100;
$X^1$ is O, S or N—R; and
R is as described above.

6. A compound according to claim 5 wherein ABT is a group represented by the chemical formula:

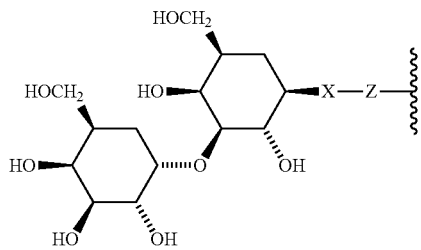

where X' is $CH_2$, O, N—$R^{1'}$, or S;
$R^{1'}$ is H or $C_1$-$C_3$ alkyl; and
Z is a bond, a monosaccharide, disaccharide or oligosaccharide.

7. A compound according to claim 1 wherein ABT is a group according to the chemical structure:

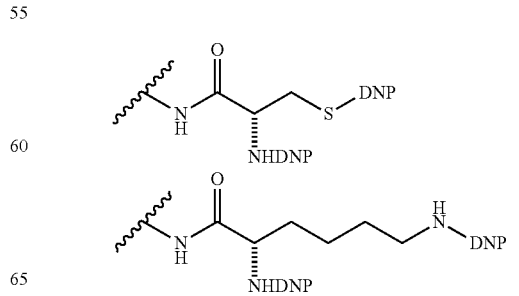

or a group according to the chemical structure:

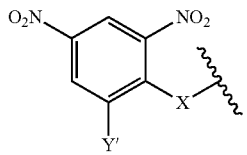

where Y' is H or $NO_2$;
X is O, $CH_2$, $NR^1$, S(O), $S(O)_2$, —$S(O)_2O$, —$OS(O)_2$, or $OS(O)_2O$; and
$R^1$ is H, a $C_1$-$C_3$ alkyl group, or a —$C(O)(C_1$-$C_3)$ group.

8. A compound according to claim 1 wherein ABT is a group according to the chemical structure:

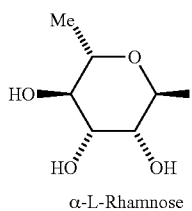

α-L-Rhamnose

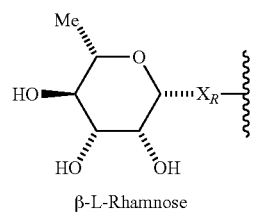

β-L-Rhamnose

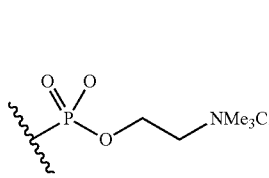

Phosphoryl Choline

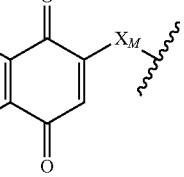

Menadione

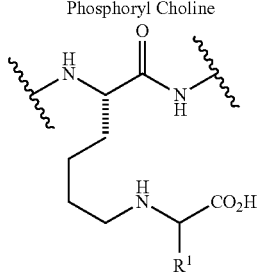

Carboxyethyl Lysine ($R^1$ = Me)

where $X_R$ is O, S or $NR^1$; and
$X_M$ is O, $NR^1$ or S, and
$R^1$ is H or a $C_1$-$C_3$ alkyl group.

9. A compound according to claim 1 wherein ABT is a rhamnose group.

10. A compound according to claim 1 wherein ABT is a group according to the chemical structure:

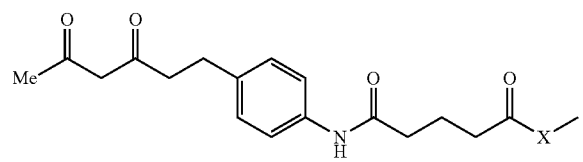

where X" is O, $CH_2$, $NR^1$, S; and
$R^1$ is H, a $C_1$-$C_3$ alkyl group or a —$C(O)(C_1$-$C_3)$ group; or

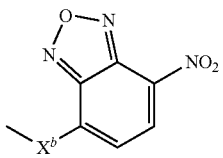

where $X^b$ is a bond, O, $CH_2$ or $NR^1$ or S; and
$R^1$ is the same as above; or
a group according to the chemical structure:

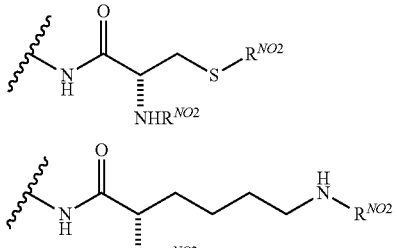

where $R^{NO2}$ is a dinitrophenyl group optionally linked through $CH_2$, S(O), $S(O)_2$, —$S(O)_2O$, —$OS(O)_2$, or $OS(O)_2O$; or
a dinitrophenyl group according to the chemical structure:

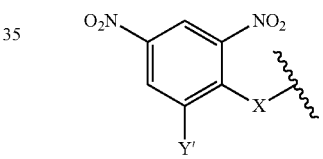

where Y' is H or $NO_2$;
X is O, $CH_2$, $NR^1$, S(O), $S(O)_2$, —$S(O)_2O$, —$OS(O)_2$, or $OS(O)_2O$; and
$R^1$ is H, a $C_1$-$C_3$ alkyl group, or a —$C(O)(C_1$-$C_3)$ group.

11. A compound according to claim 1 wherein ABT is a dinitrophenyl group or a rhamnose group.

12. A compound according to claim 1 wherein LINKER covalently attaches to TBT or ABT through a CT group according to the chemical structure:

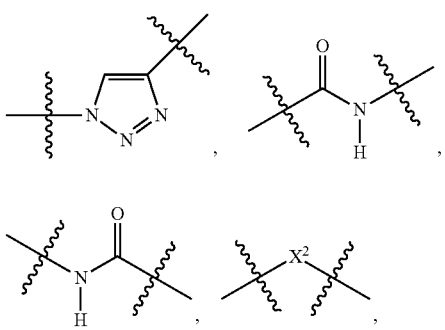

-continued

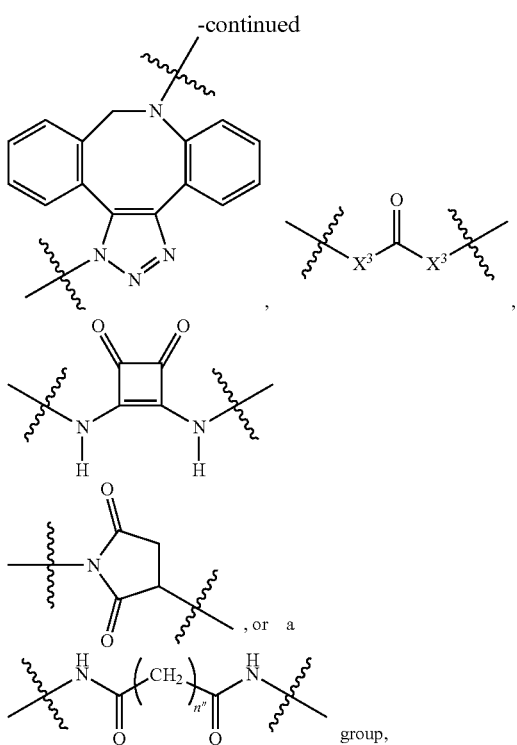

where $X^2$ is $CH_2$, O, S, $NR^4$, S(O), $S(O)_2$, —$S(O)_2O$, —$OS(O)_2$, or $OS(O)_2O$;

$X^3$ is O, S, $NR^4$;

$R^4$ is H, a $C_1$-$C_3$ alkyl or alkanol group, or a —C(O)($C_1$-$C_3$) group; and n" is independently 1 to 8.

13. A pharmaceutical composition comprising an effective amount of a compound according to claim 1 and a pharmaceutically acceptable carrier.

14. The composition according to claim 13 comprising an additional anti-cancer agent.

15. A method of treating cancer in a patient in need thereof comprising administering to said patient an effective amount of a compound according to claim 1.

16. The method according to claim 15 wherein said cancer is a metastatic cancer, a recurrent cancer or a drug resistant, including multiple drug resistant cancer.

17. The method according to claim 16 wherein said cancer is prostate cancer, metastatic prostate cancer or recurrent prostate cancer.

18. A method of reducing the likelihood that a cancer in a patient will metastasize comprising administering to said cancer patient a compound according to claim 1.

19. A compound according to the chemical structure:

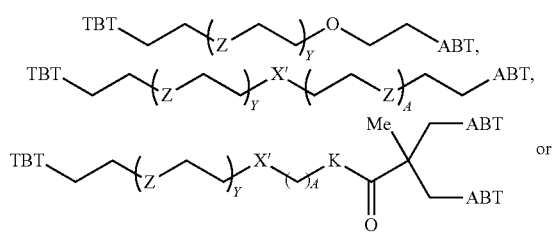

-continued

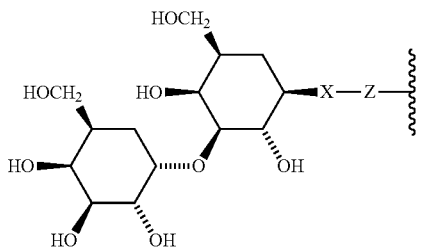

Wherein ABT is an antibody binding moiety comprising a hapten which is capable of binding to an antibody in said patient or subject wherein ABT is a group according to the chemical formula:

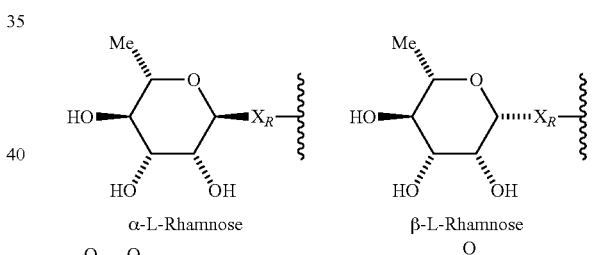

where X is $CH_2$, O, N—$R^{1'}$, or S;

$R^{1'}$ is H or $C_1$-$C_3$ alkyl; and

Z is a bond, a monosaccharide, disaccharide or oligosaccharide, or

ABT is a group according to the chemical formula:

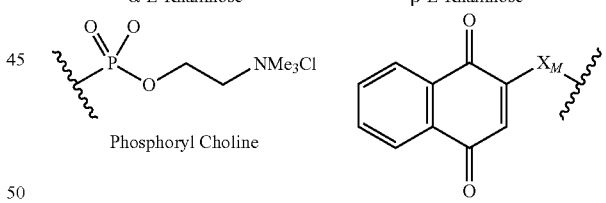

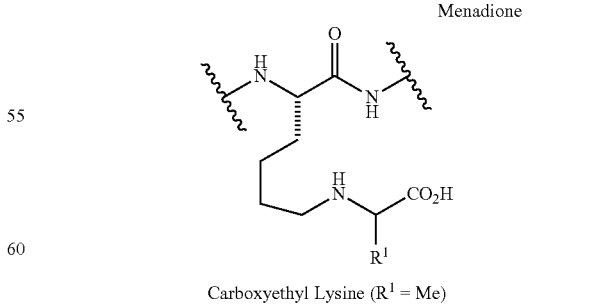

where $X_R$ is O, S or $NR^1$; and $X_M$ is O, $NR^1$ or S, and $R^1$ is H or a $C_1$-$C_3$ alkyl group, or ABT is a group according to the chemical formula:

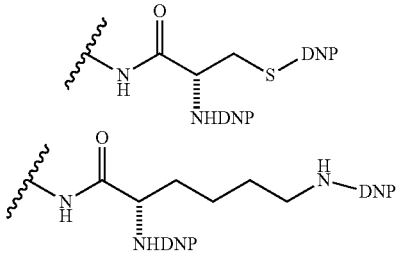

or a group according to the chemical formula:

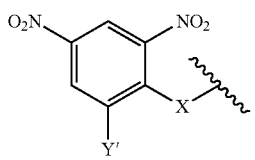

where Y' is H or $NO_2$;
X is O, $CH_2$, $NR^1$, S(O), $S(O)_2$, —$S(O)_2O$, —$OS(O)_2$, or $OS(O)_2O$; and
$R^1$ is H, a $C_1$-$C_3$ alkyl group, or a —$C(O)(C_1$-$C_3)$ group, or
ABT is a group according to the chemical formula:

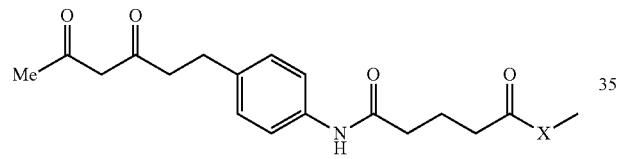

where X" is O, $CH_2$, $NR^1$, S; and
$R^1$ is H, a $C_1$-$C_3$ alkyl group or a —$C(O)(C_1$-$C_3)$ group; or

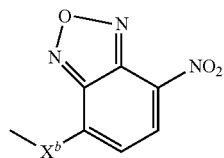

where $X^b$ is a bond, O, $CH_2$ or $NR^1$ or S; and
$R^1$ is the same as above; or
ABT is a group according to the chemical structure:

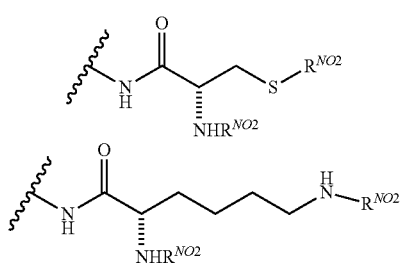

where $R^{NO2}$ is a dinitrophenyl group optionally linked through $CH_2$, S(O), $S(O)_2$, —$S(O)_2O$, —$OS(O)_2$, or $OS(O)_2O$; or
a dinitrophenyl group according to the chemical structure:

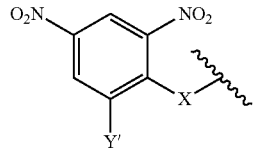

where Y' is H or $NO_2$;
X is O, $CH_2$, $NR^1$, S(O), $S(O)_2$, —$S(O)_2O$, —$OS(O)_2$, or $OS(O)_2O$; and
$R^1$ is H, a $C_1$-$C_3$ alkyl group, or a —$C(O)(C_1$-$C_3)$ group;
TBT is a group according to the chemical structure:

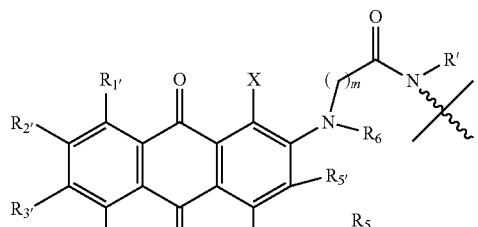

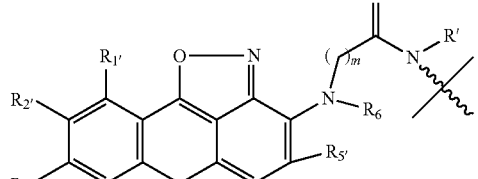

wherein X=H, F, Cl, Br, $CF_3$, $MeSO_2$, $CH_3O$, $CFO_3O$
$N(R^N)_2$, where each $R^N$ is independently H or a $C_1$-$C_3$ alkyl group;
$R_1$, $R_2$, $R_3$, $R_4$ and $R_5$ are each independently H, a halogen, a $C_1$-$C_3$ alkyl group optionally substituted with one or two hydroxyl groups or up to three fluoro groups, $NO_2$, CN, a $(CH_2)_m OR^E$ (O-alkyl) group, a $(CH_2)_m COR^E$ (keto) group, a $(CH_2)_m COOR^E$ (carboxy ester) group, a $(CH_2)_m SO_3H$ group, a $(CH_2)_m OCOR^E$ (oxycarbonyl ester) group,

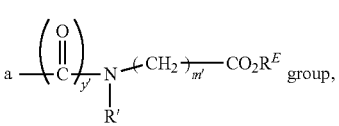 group,

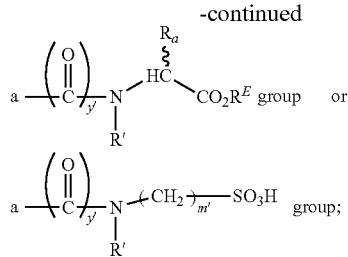

Each R' is independently H or a $C_1$-$C_3$ alkyl group;
$R_a$ is a sidechain of a natural or unnatural amino acid (D- or L-) wherein said amino acid is selected from the group consisting of alanine wherein said sidechain is methyl, arginine wherein said sidechain is propyleneguanidine, asparagine wherein said sidechain is methylenecarboxyamide, aspartic acid wherein said sidechain is ethanoic acid, cysteine wherein said sidechain is thiol or di-thiol, glutamine wherein said sidechain is ethylcarboxyamide, glutamic acid wherein said sidechain is propanoic acid, histidine wherein said sidechain is methyleneimidazole, isoleucine wherein said sidechain is 1-methylpropane, leucine wherein said sidechain is 2-methylpropane, lysine wherein said sidechain is butyleneamine, methionine wherein said sidechain is ethylmethylthioether, phenylalanine wherein said sidechain is benzyl, proline wherein said sidechain $R_a$ forms a cyclic ring with R' and the adjacent nitrogen group to form a pyrrolidine group, hydroxyproline wherein said sidechain $R_a$ forms a cyclic ring with R' and the adjacent nitrogen group to form a hydroxypyrrolidine group, serine wherein said sidechain is methanol, threonine wherein said sidechain is 1-hydroxyethane, tryptophan wherein said sidechain is methyleneindole, tyrosine wherein said sidechain is methylene phenol or valine wherein said sidechain is isopropyl;
Each $R^E$ is independently H or a $C_1$-$C_6$ alkyl group optionally substituted with one or two hydroxyl groups or up to three chloro or fluoro groups;
$R_{1'}$, $R_{2'}$, $R_{3'}$, $R_{4'}$ and $R_{5'}$ are each independently H, a halogen, a $C_1$-$C_6$ alkyl group optionally substituted with one or two hydroxyl groups or up to three chloro or fluoro groups, $NO_2$, CN, a $(CH_2)_m OR^E$ (O-alkyl) group, a $(CH_2)_m COOR^E$ (carboxy ester) group, a $(CH_2)_m O$—$COR^E$ (oxycarbonyl ester) group or a $(CH_2)_m COR^E$ (keto) group;
Each m' is independently 0, 1, 2, 3, 4, 5, or 6;
Each y' is independently 0, 1 or 2;
m=0-5, and
$R_6$=H, $C_1$-$C_4$ lower alkyl;
Z is $CH_2$ or O;
K and $K_1$ are each independently O or $NR_3$;
$R_3$ is H or $C_1$-$C_3$ alkyl;
Y is 1-6;
A is 0-3;
X' is $CH_2$, O,

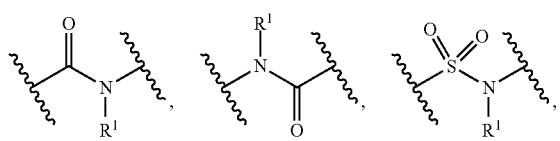

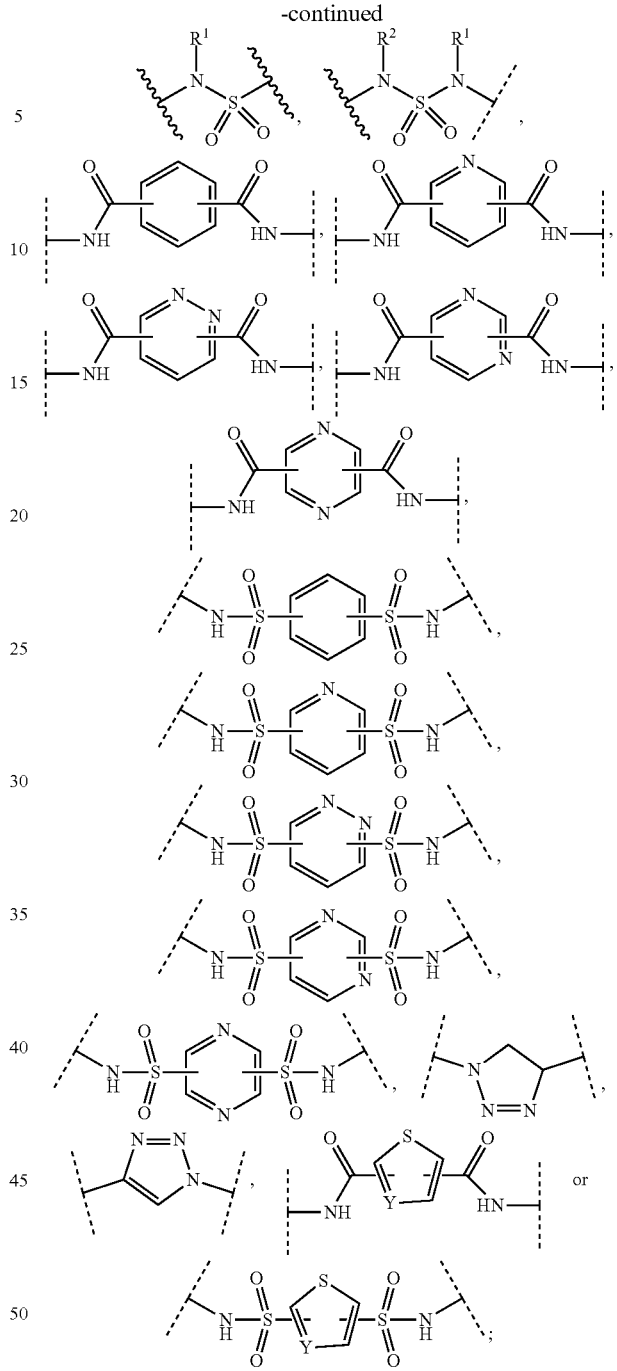

and
$R^1$ and $R^2$ are each independently H, $C_1$-$C_3$ alkyl, hydroxylalkyl and amino alkyl, or
a pharmaceutically acceptable salt, stereoisomer or enantiomer thereof.

20. The compound according to claim 19 wherein $R_1$ is H or $SO_3H$, $R_2$ is H, $CO_2H$, $SO_3H$, —$NHCH_2$—$CO_2H$, —$NHCH_2$—$SO_3H$, —C(O)—$NHCH_2$—$C_2H$ or —C(O)—$NHCH_2$—$SO_3H$, $R_3$ is H, $CO_2H$, or $SO_3H$, $R_4$ is H, $CO_2H$, or $SO_3H$, and $R_5$ is H, $CO_2H$, or $SO_3H$.

\* \* \* \* \*